US006824987B1

(12) United States Patent
Schreiber et al.

(10) Patent No.: US 6,824,987 B1
(45) Date of Patent: Nov. 30, 2004

(54) SMALL MOLECULE PRINTING

(75) Inventors: Stuart L. Schreiber, Boston, MA (US); Gavin MacBeath, Arlington, MA (US); Angela N. Koehler, Cambridge, MA (US); Paul Hergenrother, Medford, MA (US); Kristopher M. Depew, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/567,910

(22) Filed: May 10, 2000

Related U.S. Application Data

(60) Provisional application No. 60/133,595, filed on May 11, 1999.

(51) Int. Cl.[7] ..................... G01N 33/53; G01N 33/543
(52) U.S. Cl. .................. 435/7.1; 435/287.1; 435/287.2; 435/288.4; 436/501; 436/518; 436/809
(58) Field of Search ............................. 435/7.1, 287.1, 435/287.2, 288.4; 436/501, 518, 809

(56) References Cited

U.S. PATENT DOCUMENTS

| | | | |
|---|---|---|---|
| 4,937,188 A | 6/1990 | Giese et al. | 435/41 |
| 5,011,770 A | 4/1991 | Kung et al. | 435/6 |
| 5,412,087 A | 5/1995 | McGall et al. | 536/24.3 |
| 5,565,324 A | 10/1996 | Still et al. | 435/6 |
| 5,599,695 A | 2/1997 | Pease et al. | 435/91.1 |
| 5,620,850 A | 4/1997 | Bamdad et al. | 530/300 |
| 5,622,826 A | 4/1997 | Varma | 435/6 |
| 5,738,990 A | 4/1998 | Edwards et al. | 435/6 |
| 5,763,263 A | 6/1998 | Dehlinger et al. | 435/287 |
| 5,770,455 A | 6/1998 | Cargill et al. | 436/518 |
| 5,807,522 A | 9/1998 | Brown et al. | 422/50 |
| 5,831,070 A | 11/1998 | Pease et al. | 536/25.3 |
| 5,846,722 A | 12/1998 | Kauvar et al. | 435/6 |
| 5,858,804 A | 1/1999 | Zanzucchi et al. | 436/536 |
| 5,876,946 A | 3/1999 | Burbaum et al. | 435/7.1 |
| 5,912,342 A | 6/1999 | Heinonen et al. | 540/139 |
| 5,919,626 A | 7/1999 | Shi et al. | 435/6 |
| 5,958,430 A | 9/1999 | Campbell et al. | 424/400 |
| 5,962,736 A | 10/1999 | Zambias et al. | 564/152 |
| 5,985,551 A | 11/1999 | Brennan | 435/6 |
| 6,020,047 A | 2/2000 | Everhart | 428/209 |
| 6,027,890 A | 2/2000 | Ness et al. | 435/6 |
| 6,048,623 A | 4/2000 | Everhart et al. | 428/464 |
| 6,331,441 B1 * | 12/2001 | Balch et al. | 436/518 |

FOREIGN PATENT DOCUMENTS

| | | |
|---|---|---|
| WO | WO 95/35505 | 12/1995 |
| WO | WO 97/19749 | 6/1997 |
| WO | WO 98/46551 | 10/1998 |
| WO | WO 98/55866 | 12/1998 |

OTHER PUBLICATIONS

Macbeath et al., Science vol. 289 (9/2000) pp. 1760–1763.*
Macbeath et al. JACS vol. 121 (8/99) pp. 7967–7968.*
U.S patent application Ser. No. 08/951,930, Schreiber et al., filed Oct. 1997.
Amara et al., "A versatile synthetic dimerizer for the regulation of protein–protein interactions" *Proc. Natl. Acad. Sci. USA* 94(20):10618–10623, 1997.
Brown, http://cmgm.stanford.edu/pbrown/mguide/index.html.
Chaiet et al., *Arch. Biochem. Biophys.* 106:1–5, 1964.
Clive et al., *Tetrahedron Lett.* 32(49):7159–7160, 1991.
Czarnik, "Encoding methods for combinatorial chemistry" *Curr. Opin. Chem. Bio.* 1:60–66, 1997.
Dobbs et al., *Chem. Eng. News* 68(17):2, 1990.
Erickson, *Chem. Eng. News* 68(33):2, 1990.
Furka et al., *Abstract 14th Int. Congr. Biochem.*, Prague, Czechoslovakia, 5:47, 1988.
Furka et al., "General method for rapid synthesis of multi-component peptide mixtures" *Int. J. Pept. Protein Res.* 37:487–493, 1991.
Hergenrother et al., "Small–Molecule Microarrays: Covalent Attachment and Screening of Alcohol–Containing Small Molecules on Glass Slides" *J. Am Chem. Soc.* XX:XX–XX, submitted.
Holt et al., *J. Am. Chem. Soc.* 115:9925–9938, 1993.
Islam et al., *J. Med. Chem.* 37:293–304, 1994.

(List continued on next page.)

*Primary Examiner*—Bennett Celsa
(74) *Attorney, Agent, or Firm*—Brenda Herschback Jarrell; C. Hunter Baker; Choate, Hall & Stewart

(57) ABSTRACT

The present invention provides compositions and methods to facilitate the identification of compounds that are capable of interacting with a biological macromolecule of interest. In one aspect, a composition is provided that comprises an array of one or more types of chemical compounds attached to a solid support, wherein the density of the array of compounds is at least 1000 spots per $cm^2$. In particularly preferred embodiments, these compounds are attached to the solid support through a covalent interaction. In general, these inventive arrays are generated by: (1) providing a solid support, wherein said solid support is functionalized with a selected chemical moiety capable of interacting with a desired chemical compound to form an attachment; (2) providing one or more solutions of one or more types of compounds to be attached to the solid support; and (3) delivering said one or more types of compounds to the solid support, whereby an array is formed and the array of compounds has a density of at least 1000 spots per $cm^2$. In another aspect, the present invention provides methods for utilizing these arrays to identify small molecule partners for biological macromolecules of interest comprising: (1) providing an array of compounds, wherein the array has a density of at least 1000 spots per $cm^2$; (2) contacting the array with one of more types of biological macromolecules of interest; and (3) determining the interaction of specific small molecule-biological macromolecule partners.

9 Claims, 18 Drawing Sheets

OTHER PUBLICATIONS

Janolino et al., "Immobilization of Proteins on Thionyl Chloride–Activated Controlled–Pore Glass" *Methods in Biotechnology, vol. 1: Immobilization of Enzymes and Cells* (Bickerstaff, ed.), Humana Press Inc., Totowa, NJ, vol. 1, pp. 21–26.

Kapoor et al., *J. Am Chem. Soc.* 120:23–29, 1998.

Keenan et al., "Synthesis and Activity of Bivalent FKBP12 Ligands for the Regulated Dimerization of Proteins" *Bioorg. Med. Chem.* 6(8):1309–35, 1998.

Lam et al., "A new type of synthetic peptide library for identifying ligand–binding activity" *Nature* 354:82–84, 1991.

Lam et al., "The 'One–Band–One–Compound' Combinatorial Library Method" *Chem Rev.* 97:411–448, 1997.

Licitra et al., *Proc. Natl. Acad. Sci. USA* 93:12817–12821, 1996.

MacBeath et al., "Printing Small Molecules as Microarrays and Detecting Protein–Ligand Interactions en Masse" *J. Am. Chem. Soc.* 121(34):7967–7968, 1999.

March, *Advanced Organic Chemistry* (4th Ed.) New York: John Wiley & Sons, 795–797, 1992.

Nestler et al., "A General Method for Molecular Tagging of Encoded Combinatorial Chemistry Libraries" *J. Org. Chem.* 59:4723–4724, 1994.

Okamoto et al., "Microarray fabrication with covalent attachment of DNA using Bubble Jet technology" *Nature Biotechnology* 18:438–441, 2000.

Panghorn et al., "Safe and Convenient Procedure for Solvent Purification" *Organometallics* 15(5):1518–1520, 1996.

Schena et al., *Science* 270:467–470, 1995.

Sebestyen et al., *Bioorg. Med. Chem. Lett.* 3:413–418, 1993.

Shalon et al., *Genome Research* 6:639–645, 1996.

Siekierka et al., *Nature* 341:755–757, 1989.

Strother et al., *J. Am. Chem. Soc.* 122:1205–1209, 2000.

Tan et al., "Stereoselective Synthesis of over Two Million Compounds Having Structural Features Both Reminiscent of Natural Products and Compatible with Miniaturized Cell-Based Assays" *J. Am. Chem. Soc.* 120:8565–8566, 1998.

Tan et al., *J. Am. Chem. Soc.* 121:9073–9087, 1999.

Woolard et al., *J. Org. Chem.* 62:6102–6103, 1997.

Wnuk, *Chem. Eng. News* 68(26):2, 1990.

* cited by examiner

Fig. 5
Chemistry Employed in Small Molecule Printing
Silylation Attachment:
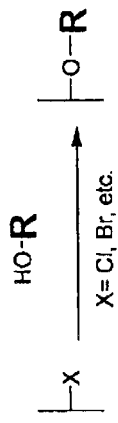
Michael Addition Attachment:
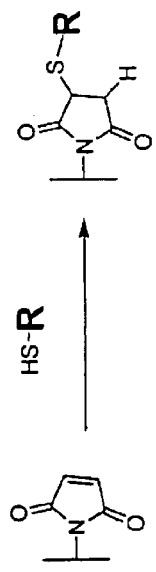
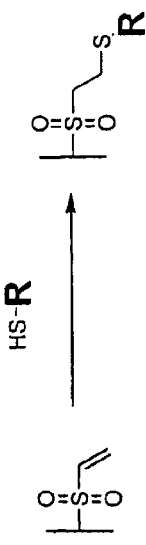
Disulfide Attachment:
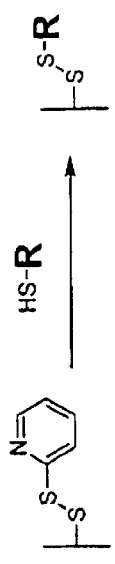
N-Hydroxy Succinimide Ester Activation:
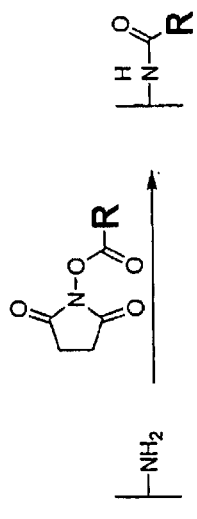
Iodoacetyl Activation:
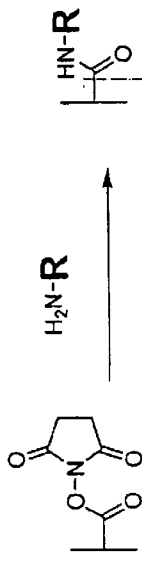
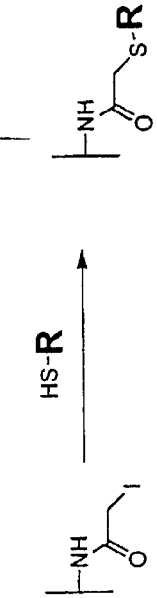
Isothiocyanate Activation:
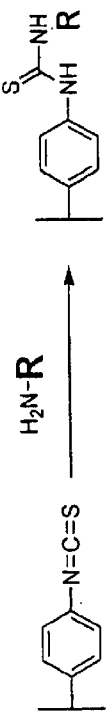

Figure 10
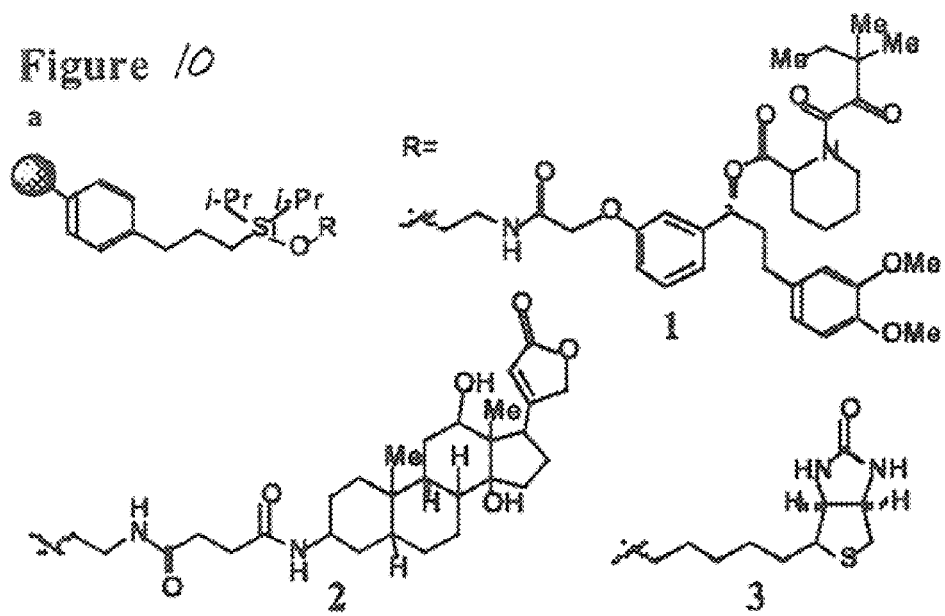
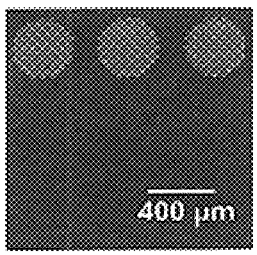
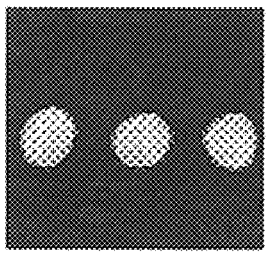
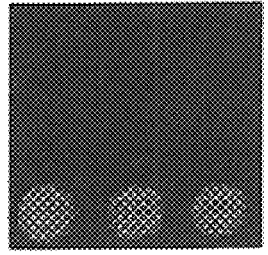
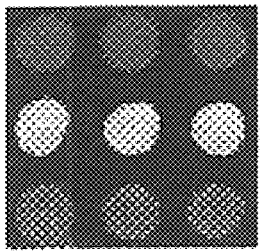
Figure 10 a) Alcohols attached to 500-560 μm polystyrene resin through a silyl-containing linker. b-e) A nine spot microarray was printed according to the pattern in 2f and visualized in the following channel(s): b) Cy5 (false-colored red), c) Cy3 (false-colored green), d) FITC (false-colored purple), e) Cy5, Cy3, and FITC. Average distance between spots = 400 μm; average spot diameter = 300 μm.

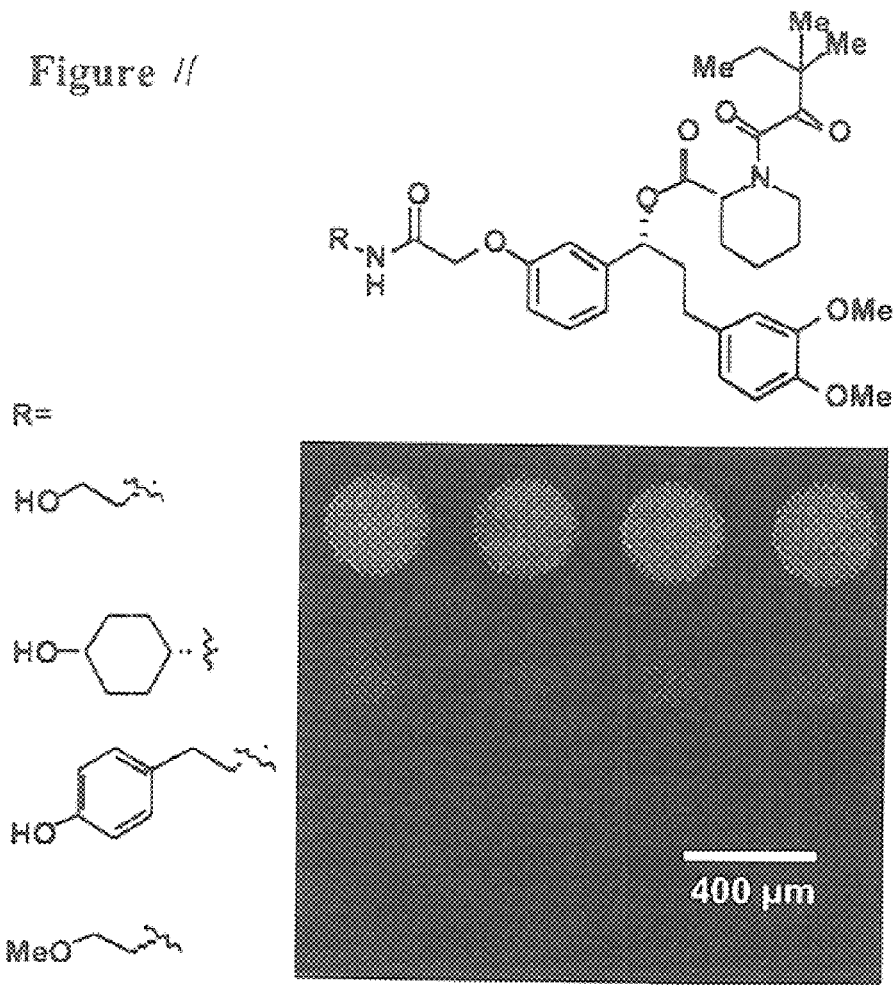
Figure 11 Microarray of primary, secondary, phenolic, and methyl ether derivatives of an FKBP ligand. Slides were probed with Cy5-labeled FKBP (false-colored red).

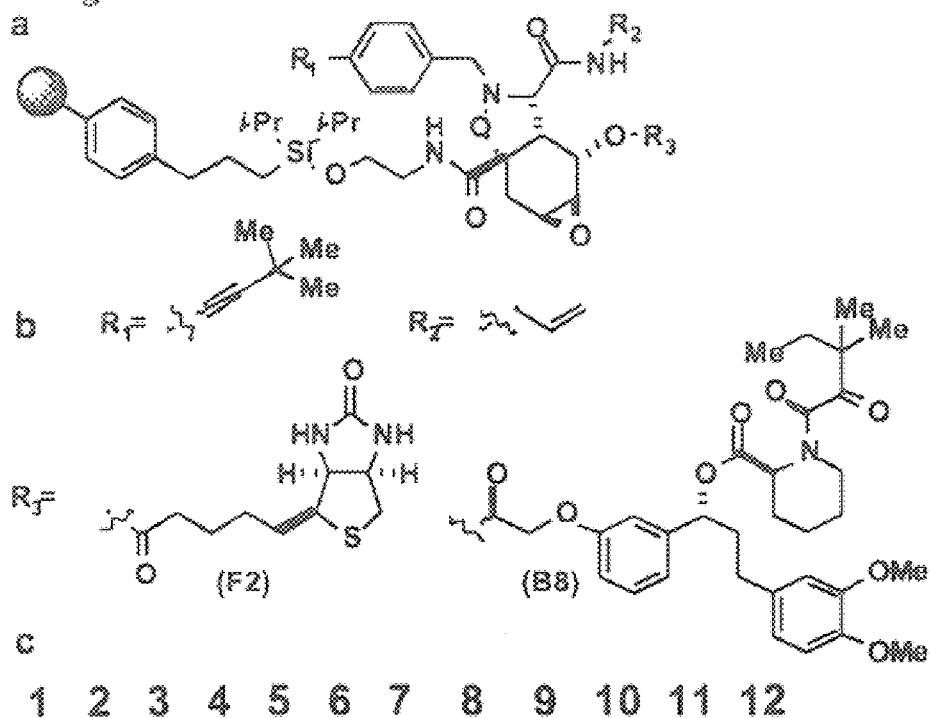
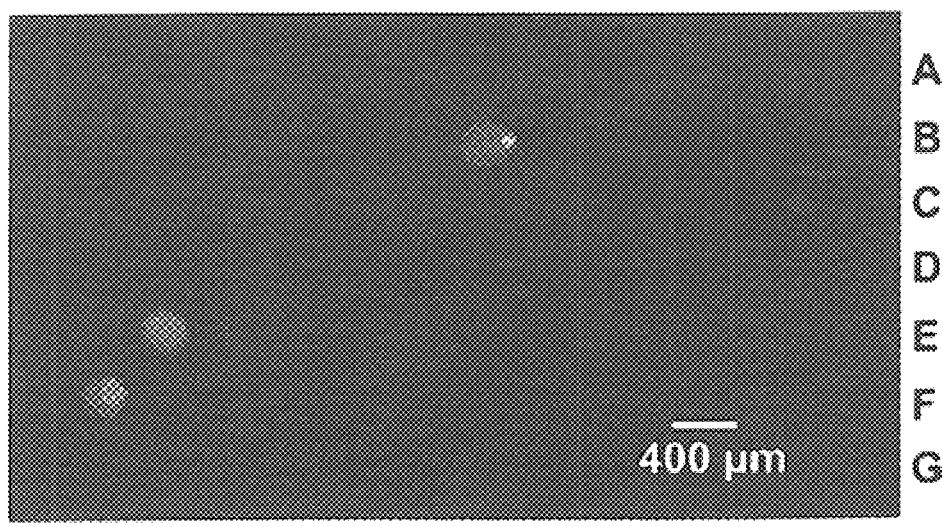

Figure 12 a) General structure of a small-molecule library, 78 members of which were placed in the wells of a 96-well plate. b) Structure of two additional 'tagged' library members. c) Alcohol microarray onto which 78 members of the small molecule library and two tagged members were printed. Protein binding detected with Cy5-FKBP (false-colored red) and FITC-streptavidin (false-colored green).

1. Add PDMS prepolymer to OmniTray (~50 g)
2. Insert master template face down into OmniTray
3. Cure polymer at 65 °C for 4 h
4. Peel PDMS polymer away from the master template To use the vessels, slides were placed face-down as illustrated below and reagent was injected under the slides with a P1000 Pipetman.

US 6,824,987 B1

SMALL MOLECULE PRINTING

RELATED APPLICATIONS

The present application claims priority to provisional application U.S. Ser. No. 60/133,595, filed May 11, 1999, which is incorporated herein by reference in its entirety.

BACKGROUND OF THE INVENTION

The ability to identify small molecule ligands for any protein of interest has far-reaching implications, both for the elucidation of protein function and for the development of novel pharmaceuticals. With the introduction of split-pool strategies for synthesis (Furka et al., *Int. J. Pept. Protein Res.* 1991, 37, 487; Lam et al., *Nature* 1991, 354, 82; each of which is incorporated herein by reference) and the development of appropriate tagging technologies (Nestler et al., *J. Org. Chem.* 1994, 59, 4723; incorporated herein by reference), chemists are now able to prepare large collections of natural product-like compounds immobilized on polymeric synthesis beads (Tan et al., *J. Am. Chem. Soc.* 1998, 120, 8565; incorporated herein by reference). These libraries provide a rich source of molecules for the discovery of new protein ligands.

With such libraries in hand, the availability of efficient methods for screening these compounds becomes imperative. One method that has been used extensively is the on-bead binding assay (Lam et al., *Chem. Rev.* 1997, 97, 411; incorporated herein by reference). An appropriately tagged protein of interest is mixed with the library and beads displaying cognate ligands are subsequently identified by a chromagenic or fluorescence-linked assay (Kapoor et al., *J. Am. Chem. Soc.* 1998, 120, 23; Morken et al., *J. Am. Chem. Soc.* 1998, 120, 30; St. Hilare et al., *J. Am. Chem. Soc.* 1998, 120, 13312; incorporated herein by reference). Despite the proven utility of this approach, it is limited by the small number of proteins that can be screened efficiently. In principle, the beads can be stripped of one protein and reprobed with another; however, this serial process is slow and limited to only a few iterations. In order to identify a specific small molecule ligand for every protein in a cell, tissue, or organism, high-throughput assays that enable each compound to be screened against many different proteins in a parallel fashion are required. Although Brown et al. (U.S. Pat. No. 5,807,522; incorporated herein by reference) have developed an apparatus and a method for forming high density arrays of biological macromolecules for large scale hybridization assays in numerous genetic applications, including genetic and physical mapping of genomes, monitoring of gene expression, DNA sequencing, genetic diagnosis, genotyping and distribution of reagents to researchers, the development of a high density array of natural product-like compounds for high-throughput screening has not been achieved.

Clearly, it would be desirable to develop methods for generating high density arrays that would enable the screening of compounds present in increasingly complex natural product-like combinatorial libraries in a high-throughput fashion to identify small molecule partners for biological macromolecules of interest.

SUMMARY OF THE INVENTION

The present invention provides compositions and methods to facilitate the high-throughput screening of compounds for the identification of desirable properties or interactions. In a preferred embodiment, the present invention provides compositions and methods to facilitate the identification of compounds that are capable of interacting with a biological macromolecule of interest. In one aspect, a composition is provided that comprises an array of more than one type of chemical compounds attached to a solid support, wherein the density of the array of compounds comprises at least 1000 spots per $cm^2$, more preferably at least 5000 spots per $cm^2$, and most preferably at least 10,000 spots per $cm^2$. In another aspect, a composition is provided that comprises a plurality of one or more types of non-oligomeric chemical compounds attached to a glass or polymer support, wherein the density of the array of compounds comprises at least 1000 spots per $cm^2$. In a particularly preferred embodiment, the chemical compounds are non-peptidic and non-oligomeric. In particularly preferred embodiments, these compounds are attached to the solid support through a covalent interaction. In another particularly preferred embodiment, small molecules are attached to the solid support through a covalent interaction. In a particularly preferred embodiment, the compounds are attached to the solid support using a Michael addition reaction. In another preferred embodiment, the compounds are attached to the solid support using a silylation reaction. In general, these inventive arrays are generated by: (1) providing a solid support, wherein said solid support is functionalized with a selected chemical moiety capable of interacting with a desired chemical compound to form an attachment; (2) providing one or more solutions of one or more types of compounds to be attached to the solid support; and (3) delivering said one or more types of compounds to the solid support whereby an array of compounds is generated and the array comprises a density of at least 1000 spots per $cm^2$ (FIG. 1). In other embodiments, the array comprises a density of at least 5000 stops per $cm^2$, and more preferably at least 10,000 spots per $cm^2$.

In another aspect, the present invention provides methods for utilizing these arrays to identify small molecule partners for biological macromolecules (e.g., proteins, peptides, polynucleotides) of interest comprising: (1) providing an array of one or more types of compounds (e.g., more preferably, small molecules), wherein the array has a density comprising at least 1000 spots per $cm^2$; (2) contacting the array with one or more types of biological macromolecules of interest; and (3) determining the interaction of specific small molecule-biological macromolecule partners (FIG. 1). In particularly preferred embodiments, the biological macromolecules of interest comprise a collection of one or more recombinant proteins. In another preferred embodiment, the biological macromolecules of interest comprise a collection of macromolecules from a cell lysate. In another preferred embodiment, the biological macromolecules of interest comprise a polynucleotide.

DEFINITIONS

Unless indicated otherwise, the terms defined below have the following meanings:

"Antiligand": As used herein, the term "antiligand" refers to the opposite member of a ligand/anti-ligand binding pair. The anti-ligand may be, for example, a protein or other macromolecule receptor in an effector/receptor binding pair.

"Compound": The term "compound" or "chemical compound" as used herein can include organometallic compounds, organic compounds, metals, transitional metal complexes, and small molecules. In certain preferred embodiments, polynucleotides are excluded from the definition of compounds. In other preferred embodiments, polynucleotides and peptides are excluded from the definition of compounds. In a particularly preferred embodiment, the term compounds refers to small molecules (e.g., preferably, non-peptidic and non-oligomeric) and excludes peptides, polynucleotides, transition metal complexes, metals, and organometallic compounds.

"Ligand": As used herein, the term "ligand" refers to one member of a ligand/anti-ligand binding pair, and is referred to herein also as "small molecule". The ligand or small molecule may be, for example, an effector molecule in an effector/receptor binding pair.

"Michael Addition": The term "Michael addition" refers to the reaction in which compounds containing electron-rich groups (e.g, groups containing sulfur, nitrogen, oxygen, or a carbanion) add, in the presence of base, to olefins of the from C=C—Z (including quinones), where Z is an electron-withdrawing group, such as aldehydes, ketones, esters, amides, nitriles, $NO_2$, SOR, $SO_2R$, etc.

"Microarray": As used herein, the term "microarray" is a regular array of regions, preferably spots of small molecule compounds, having a density of discrete regions of at least about $1000/cm^2$.

"Natural Product-Like Compound": As used herein, the term "natural product-like compound" refers to compounds that are similar to complex natural products which nature has selected through evolution. Typically, these compounds contain one or more stereocenters, a high density and diversity of functionality, and a diverse selection of atoms within one structure. In this context, diversity of functionality can be defined as varying the topology, charge, size, hydrophilicity, hydrophobicity, and reactivity to name a few, of the functional groups present in the compounds. The term, "high density of functionality", as used herein, can preferably be used to define any molecule that contains preferably three or more latent or active diversifiable functional moieties. These structural characteristics may additionally render the inventive compounds functionally reminiscent of complex natural products, in that they may interact specifically with a particular biological receptor, and thus may also be functionally natural product-like.

"Peptide": According to the present invention, a "peptide" comprises a string of at least three amino acids linked together by peptide bonds. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide maybe modified, for example, by the addition of a chemical entity such as a carbohydrate group, a phosphate group, a farnesyl group, an isofarnesyl group, a fatty acid group, a linker for conjugation, functionalization, or other modification, etc.

"Polynucleotide" or "oligonucleotide": Polynucleotide or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small Molecule": As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 1998, 120, 8565) and pending application Ser. No. 08/951,930 "Synthesis of Combinatorial Libraries of Compounds Reminiscent of Natural Products", the entire contents of which are incorporated herein by reference. In certain other preferred embodiments, natural-product-like small molecules are utilized.

DESCRIPTION OF THE DRAWING

FIG. 5 shows other attachment chemistries which may be used in small molecule printing.

FIG. 10 shows a) alcohols attached to 500–560 μm polystyrene resin through a silyl-containing linker; b–e) a nine spot microarray printed according to the pattern in 6f and visualized in the following channels: b) Cy5 (false-colored red), c) Cy3 (false-colored green), d) FITC (false-colored purple), e) Cy5, Cy3, and FITC. Average distance between spots=400 μm; average spot diameter=300 μm.

FIG. 11 shows a microarray of primary, secondary, phenolic, and methyl ester derivatives of an FKBP ligand. Slides were probed with Cy5-labeled FKBP (false-colored red).

FIG. 12 shows a) the general structure of a small-molecule library, 78 members of which were placed in the wells of a 96-well plate; b) the structure of two additional 'tagged' library members; c) alcohol microarray onto which 78 members of the small molecule library and two tagged members were printed. Protein binding detected with Cy5-FKBP (false-colored red) and FITC-streptavidin (false-colored green).

DESCRIPTION OF CERTAIN PREFERRED EMBODIMENTS

Figure 1:
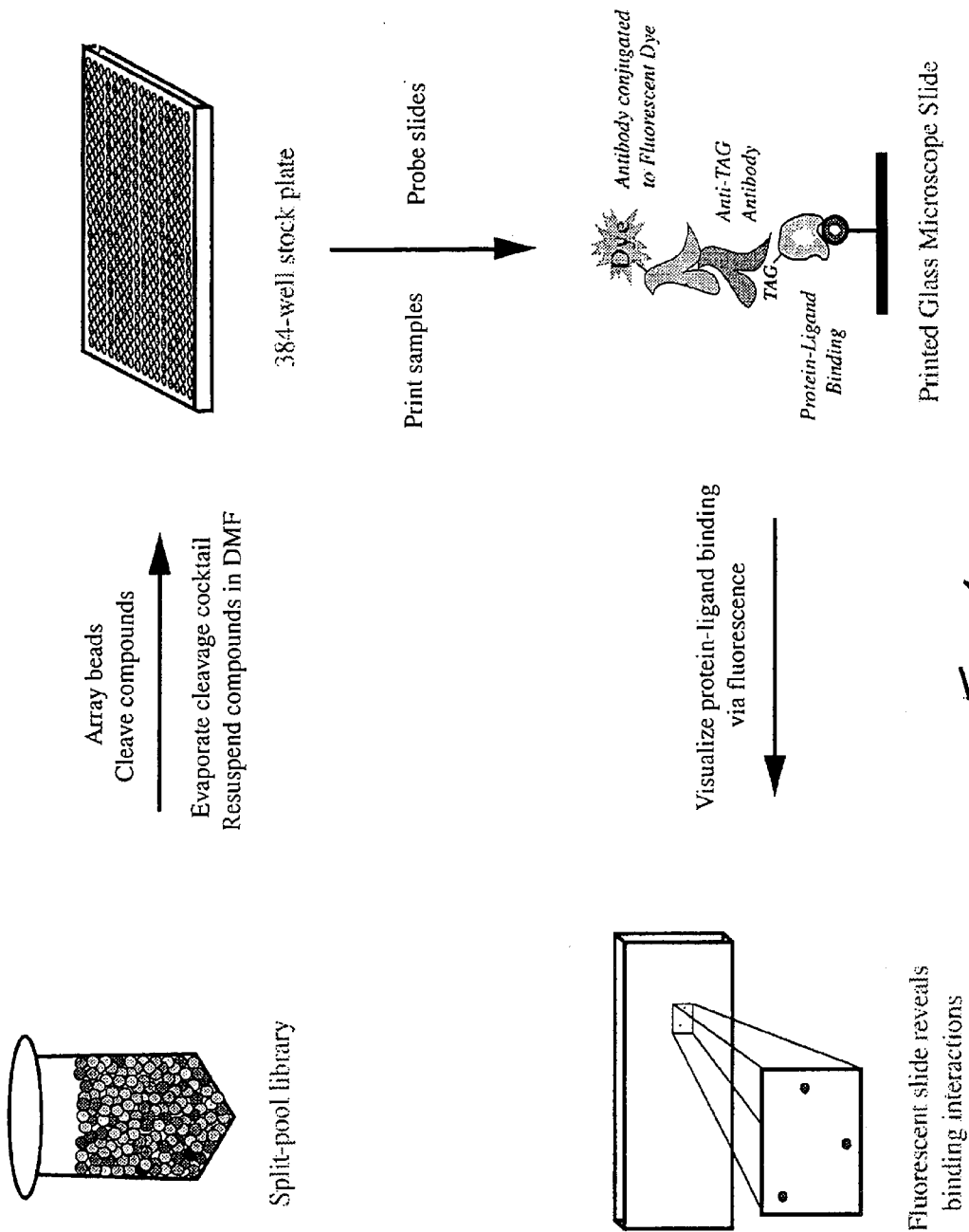
FIG. 1 depicts one preferred embodiment of the complete process of small printing and assaying for chemical compounds with desired properties. The process begins with the combinatorial library. The library is transferred to stock plates which are used to print the compounds onto glass slides. The slide is then used to assay for chemical compounds with the desired property.

As discussed above, the recent advances in the generation of complex chemical libraries of natural product-like compounds having as many as, or more than, one million members, has led to the subsequent need to facilitate the efficient screening of these compounds for biological activity. Towards this end, the present invention provides methods and compositions to enable the high-throughput screening of very large numbers of chemical compounds to identify those with desirable properties of interest. In preferred embodiments, methods and compositions are provided to enable the high-throughput screen of very large numbers of chemical compounds to identify those compounds capable of interacting with biological macromolecules.

In one aspect, the present invention provides compositions comprising arrays of chemical compounds, attached to a solid support having a density of at least 1000 spots per $cm^2$, and methods for generating these arrays. In particularly preferred embodiments, the present invention provides arrays of small molecules, more preferably natural product-like compounds, that are generated from split-and-pool synthesis techniques, parallel synthesis techniques, and traditional one-at-a time synthesis techniques. Additionally, existing collections of compounds may also be utilized in the present invention, to provide high density arrays that can be screened for desirable characteristics. In another aspect, the present invention provides methods for the identification of ligand (small molecule)-antiligand (biological macromolecule) binding pairs using the chemical compound arrays. It is particularly preferred that the antiligands comprise recombinant protein, and it is more particularly preferred that a library of recombinant proteins is utilized in the detection method. In another preferred embodiment, the antiligands comprise macromolecules from cell lysates.

Small Molecule Printing

As discussed above, in one aspect, the present invention provides methods, referred to herein as "small molecule printing", for the generation of high density arrays and the resulting compositions. According to the method of the present invention, a collection of chemical compounds, or one type of compound, can be "printed" onto a support to generate extremely high density arrays. In general, this method comprises (1) providing a solid support, wherein the solid support is functionalized with a selected chemical moiety capable of interacting with a desired chemical compound to form an attachment; (2) providing one or more solutions of the same or different chemical compounds to be attached to the solid support; and (3) delivering the one or more solutions of the same or different chemical compounds to the solid support, whereby an array of compounds is generated and the array has a density of at least 1000 spots per $cm^2$.

As one of ordinary skill in the art will realize, although any desired chemical compound capable of forming an attachment with the solid support may be utilized, it is particularly preferred that natural product-like compounds, preferably small molecules, generated from split-and-pool library or parallel syntheses are utilized. Examples of libraries of natural product like compounds that can be utilized in the present invention include, but are not limited to shikimic acid-based libraries, as described in Tan et al. ("Stereoselective Synthesis of over Two Million Compounds Having Structural Features Both Reminiscent of Natural Products and Compatible with Miniaturized Cell-Based Assays", *J. Am. Chem. Soc.*, 1998, 120, 8565) and incorporated herein by reference. As will be appreciated by one of ordinary skill in the art, the use of split-and-pool libraries enables the more efficient generation and screening of compounds. However, small molecules synthesized by parallel synthesis methods and by traditional methods (one-at-a-time synthesis and modifications of these structures) can also be utilized in the compositions and methods of the present invention, as can naturally occurring compounds, or other collections of compounds, preferably non-oligomeric compounds, that are capable of attaching to a solid support without further synthetic modification.

As will be realized by one of ordinary skill in the art, in split-and-pool techniques (see, for example, Furka et al., *Abstr. 14th Int. Congr. Biochem.*, Prague, Czechoslovakia, 1988, 5, 47; Furka et al., *Int. J. Pept. Protein Res.* 1991, 37, 487; Sebestyen et al., *Bioorg. Med. Chem. Lett.* 1993, 3, 413; each of which is incorporated herein by reference), a mixture of related compounds can be made in the same reaction vessel, thus substantially reducing the number of containers required for the synthesis of very large libraries, such as those containing as many as or more than one million library members. As an example, a solid support bound scaffold can be divided into n vessels, where n represents the number of species of reagent A to be reacted with the support bound scaffold. After reaction, the contents from n vessels are combined and then split into m vessels, where m represents the number of species of reagent B to be reacted with the support bound scaffold. This procedure is repeated until the desired number of reagents are reacted with the scaffold structures to yield a desired library of compounds.

As mentioned above, the use of parallel synthesis methods are also applicable. Parallel synthesis techniques traditionally involve the separate assembly of products in their own reaction vessels. For example, a microtiter plate containing n rows and m columns of tiny wells which are capable of holding a small volume of solvent in which the reaction can occur, can be utilized. Thus, n variants of reactant type A can be reacted with m variants of reactant type B to obtain a library of n×m compounds.

Subsequently, once the desired compounds have been provided using an appropriate method, solutions of the desired compounds are prepared. In a preferred embodiment, compounds are synthesized on a solid support and the resulting synthesis beads are subsequently distributed into polypropylene microtiter plates at a density of one bead per well. In but one example, as discussed below in the Examples, the attached compounds are then released from their beads and dissolved in a small volume of suitable solvent. Due to the minute quantities of compound present on each bead, extreme miniaturization of the subsequent assay is required. Thus, in a particularly preferred embodiment, a high-precision transcription array robot (Schena et al., *Science* 1995, 270, 467; Shalon et al., *Genome Research* 1996, 6, 639; each of which is incorporated herein by reference) can be used to pick up a small volume of dissolved compound from each well and repetitively deliver approximately 1 nL of solution to defined locations on a series of chemically-derivatized glass microscope slides. These chemically-derivatized glass microscope slides are preferably prepared using custom slide-sized reaction vessels that enable the uniform application of solution to one face of the slide as shown and discussed in the Examples. This results in the formation of microscopic spots of compounds on the slides and in preferred embodiments these spots are 200–250 μm in diameter. It will be appreciated by one of ordinary skill in the art, however, that the current invention is not limited to the delivery of 1 nL volumes of solution and that alternative means of delivery can be used that are capable of delivering picoliter or smaller volumes. Hence, in addition to a high precision transcription array robot, other means for delivering the compounds can be used, including, but not limited to, ink jet printers, piezoelectric printers, and small volume pipetting robots.

As discussed, each compound contains a common functional group that mediates attachment to a support surface. It is preferred that the attachment formed is robust and therefore the formation of covalent attachments are particularly preferred. A variety of chemical linkages can be employed to generate the high density arrays of chemical compounds. In addition to the robustness of the linkage, other considerations include the solid support to be utilized and the specific class of compounds to be attached to the support. Particularly preferred supports include, but are not limited to glass slides, polymer supports or other solid-material supports, and flexible membrane supports.

Figure 2:
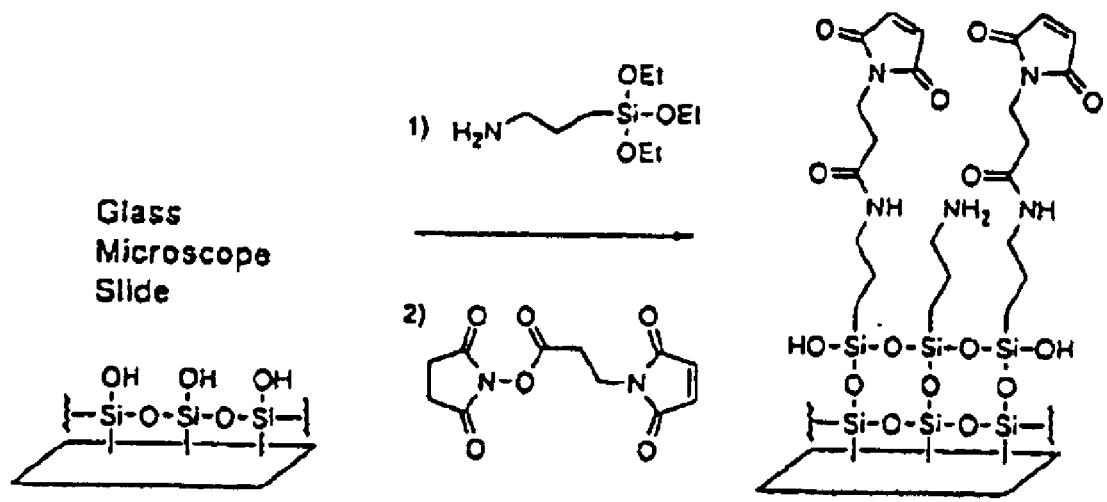
FIG. 2 depicts the preparation of maleimide-derivatized glass slides.

In but one example, and as discussed in Example 1, a Michael addition (March, *Advanced Organic Chemistry* (4th ed.), New York: John Wiley & Sons, 1992, 795–797; incorporated herein by reference) can be employed to attach compounds to glass slides. In one embodiment, as shown in FIG. 2, plain glass slides are derivatized to give surfaces that are densely functionalized with maleimide groups. Compounds containing thiol groups can then be provided. These thiol-containing compounds readily attach to the surface upon printing via the expected thioether linkage. As one of ordinary skill in the art will realize, other nucleophilic S-, N-, and O-containing compounds can be generated to facilitate attachment of the chemical compound to the solid support via Michael addition, as described above. Other electrophilic Michael acceptors can also be utilized; however, maleimides and vinyl sulfones are particularly preferred because the hydrophilicity of these groups is believed to play a role in the observed lack of nonspecific protein binding to the slide surface in aqueous buffer.

In another example, and as discussed in Example 2, a silylation reaction can be employed to attach compounds to a glass slide. Plain glass slides are derivatized to yield surfaces that are densely functionalized with silyl halides. Compounds containing hydroxyl groups can then be provided and contacted with the functionalized glass surface. The hydroxyl containing compounds readily attach to the surface through the silicon-oxygen bond formed by nucleophilic substitution on the silyl halide. In a preferred embodiment, the silyl halide is silyl chloride, bromide, or iodide. In other preferred embodiments, leaving groups on the silicon such as mesylate and tosylate are used rather than halide. Preferably, the hydroxyl groups of the compounds to be attached are unhindered (e.g., primary alcohols).

Figure 3:
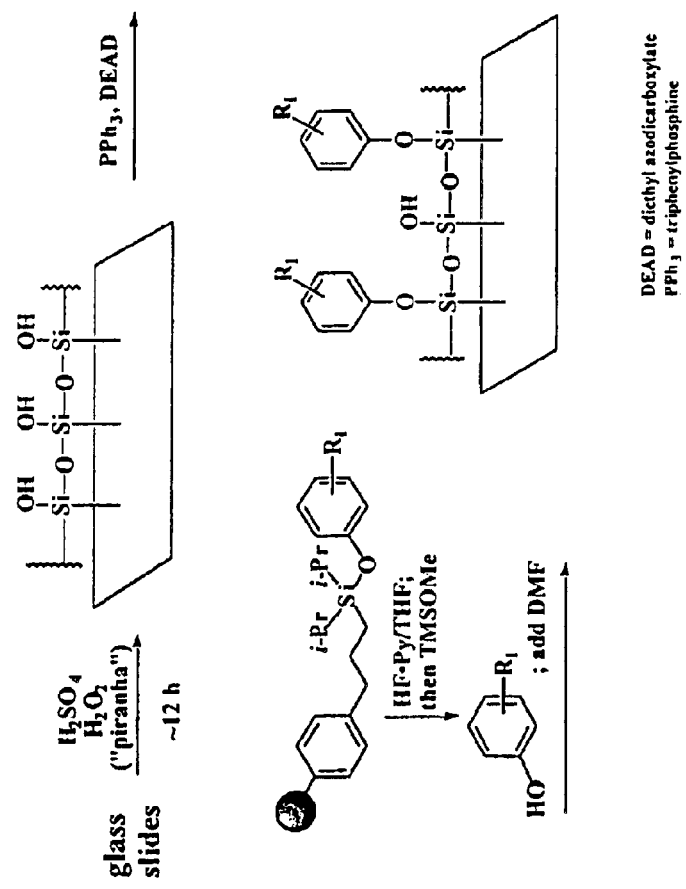
FIG. 3 shows the attachment of phenolic hydroxyl groups using a Mitsunobu activation of the glass surface.
Figure 4:
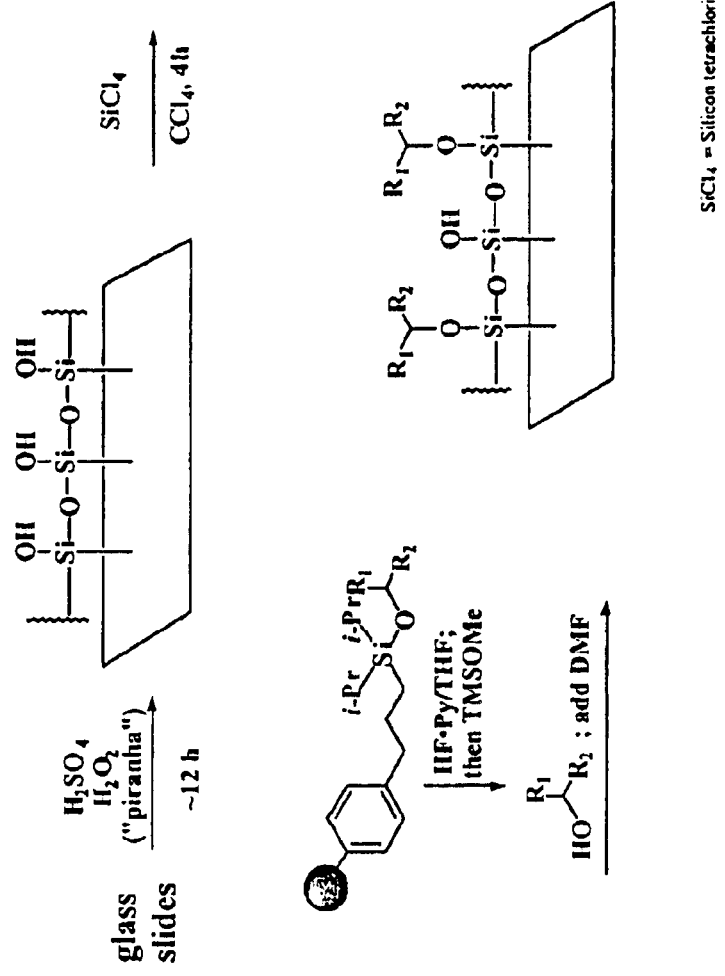
FIG. 4 shows the attachment of compounds having a secondary alcohol to a silicon tetrachloride-activated glass surface.

In another preferred embodiment, compounds with phenolic hydroxyl groups are attached to a glass surface using Mitsunobu activation of the surface as shown in FIG. 3 (Derrick et al., *Tetrahedron Lett.* 1991, 32, 7159; incorporated herein by reference). In yet another preferred embodiment, compounds with secondary alcohols are attached a glass surface activated with silicon tetrachloride (FIG. 4).

Other linkages (FIG. 5) that can be employed in the preparation of the inventive arrays include, but are not limited to disulfide bonds, amide bonds, ester bonds, ether bonds, hydrazone linkages, carbon-carbon bonds, metal ion complexes, and noncovalent linkages mediated by, for example, hydrophobic interactions or hydrogen bonding. In certain preferred embodiments, coupling of acids and amines, coupling of aldehydes and hydrazide, coupling of trichlorocyanuric acid and amines, addition of amines to quinones, attachment of thiols to mercury, addition of sulfhydryls, amines, and hydroxyls to open bis-epoxides, photoreactions of azido compounds to give insertions via a nitrene intermediate, or coupling of diols to boronate is used in the preparation of the inventive arrays. It will be appreciated by one of skill in this art that the specific linkages to be utilized should be selected to be (1) robust enough so that the small molecules are not inadvertently cleaved during subsequent assaying steps, and (2) inert so that the functionalities employed do not interfere with the subsequent assaying steps.

Methods for Detecting Biological Activity

It will be appreciated by one of ordinary skill in the art that the generation of arrays of compounds having extremely high spatial densitiles facilitates the detection of binding and/or activation events occurring between compounds in a specific chemical library and biological macromolecules. Thus, the present invention provides, in yet another aspect, a method for identifying small molecule partners for biological macromolecules of interest. The partners may be compounds that bind to particular macromolecules of interest and are capable of activating or inhibiting the biological macromolecules of interest. In general, this method involves (1) providing an array of one or more types of compounds, as described above, wherein the array of small molecules has a density of at least 1000 spots per $cm^2$; (2) contacting the array with one or more types of biological macromolecules of interest; and (3) determining the interaction of specific small molecule-biological macromolecule partners.

It will also be appreciated that the arrays of the present invention may be utilized in a variety of ways to enable detection of interactions between small molecules and biological macromolecules. In one particularly preferred embodiment, an array of different types of chemical compounds attached to the surface is utilized and is contacted by one or a few types of biological macromolecules to determine which compounds are capable of interacting with the specific biological macromolecule(s). As one of ordinary skill in the art will realize, if more than one type of compound is utilized, it is desirable to utilize a method for encoding each of the specific compounds so that a compound having a specific interaction can be identified. Specific encoding techniques have been recently reviewed and these techniques, as well as other equivalent or improved techniques, can be utilized in the present invention (see, Czarnik, A. W. *Current Opinion in Chemical Biology* 1997, 1, 60; incorporated herein by reference). Alternatively the arrays of the present invention may comprise one type of chemical compound and a library of biological macromolecules may be contacted with this array to determine the ability of this one type of chemical compound to interact with a variety of biological macromolecules. As will be appreciated by one of ordinary skill in the art, this embodiment requires the ability to separate regions of the support, utilizing paraffin or other suitable materials, so that the assays are localized.

As one of ordinary skill in the art will realize, the biological macromolecule of interest may comprise any biomolecules. In preferred embodiments, the biological macromolecule of interest comprises a protein, and more preferably the array is contacted with a library of recombinant proteins of interest. In yet another preferred embodiment, the biological molecules of interest are provided in the form of cell lysates such as those of tumor-associated cells. As will be appreciated by one of ordinary skill in the art, these proteins may comprise purified proteins, pools of purified proteins, and complex mixtures such as cell lysates, and fractions thereof, to name a few. Examples of particularly preferred biological macromolecules to study include, but are not limited to those involved in signal transduction, dimerization, gene regulation, cell cycle and cell cycle checkpoints, and DNA damage checkpoints. Furthermore, the ability to construct libraries of expressed proteins from any organism or tissue of interest will lead to large arrays of recombinant proteins. The compounds of interest may be capable of either inactivating or activating the function of the particular biomolecules of interest.

Each of the biological macromolecules may be modified to enable the facile detection of these macromolecules and the immobilized compounds. This may be achieved by tagging the macromolecules with epitopes that are subsequently recognized, either directly or indirectly, by a different receptor (e.g., an antibody) that has been labeled for subsequent detection (e.g., with radioactive atoms, fluorescent molecules, colored compounds, or enzymes that enable color formation, or light production, to name a few). Alternatively, the macromolecules themselves may be labeled directly using any one or other of these methods or not labeled at all if an appropriate detection method is used to detect the bound protein (e.g., mass spectrometry, surface plasmon resonance, and optical spectroscopy, to name a few).

In a particularly preferred embodiment, the inventive arrays are utilized to identify compounds for chemical genetic research. In classical genetics, either inactivating (e.g., deletion or "knock-out") or activating (e.g., oncogenic) mutations in DNA sequences are used to study the function of the proteins that are encoded by these genes. Chemical genetics instead involves the use of small molecules that alter the function of proteins to which they bind, thus either inactivating or activating protein function. This, of course, is the basis of action of most currently approved small molecule drugs. The present invention involves the development of "chip-like" technology to enable the rapid detection of interactions between small molecules and specific proteins of interest. The examples presented below demonstrate how the methods and compositions of the present invention can be used to identify new small molecule ligands for use in chemical genetic research. One of ordinary skill in the art will realize that the inventive compositions and methods can be utilized for other purposes that require a high density chemical compound format.

As will also be appreciated by one of ordinary skill in the art, arrays of chemical compounds may also be useful in detecting interactions between the compounds and alternate classes of molecules other than biological macromolecules. For example, the arrays of the present invention may also be useful in the fields of catalysis and materials research to name a few.

These and other aspects of the present invention will be further appreciated upon consideration of the following Examples, which are intended to illustrate certain particular embodiments of the invention but are not intended to limit its scope, as defined by the claims.

EXAMPLES

Example 1

Small Molecule Printing Using Michael Addition

Figure 6:
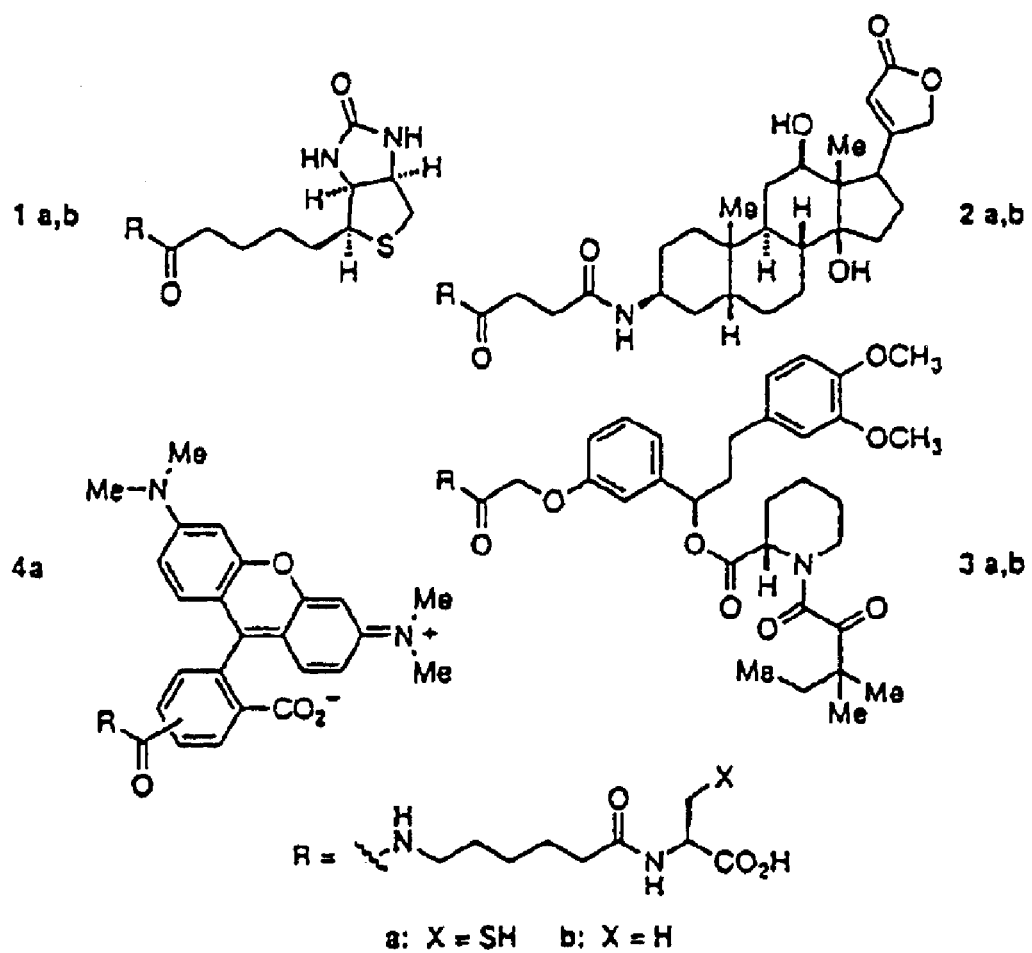
FIG. 6 depicts test compounds used to demonstrate the concept of small molecule printing.

In order to demonstrate the utility of small molecule printing as a technique identifying small molecule-protein interactions, three unrelated molecules were chosen for which specific protein receptors are available. Compound 1 (FIG. 6, R=OH) is the vitamin biotin, which is recognized by the bacterial protein streptavidin (Chaiet et al., *Arch. Biochem. Biophys.* 1964, 106, 1; incorporated herein by reference). Compound 2 (R=OH) is a derivative of the steroid digoxigenin and is recognized by the mouse monoclonal antibody DI-22 (Sigma). Finally, compound 3 (R=OH) is a synthetic pipecolyl α-ketoamide, which was designed to be recognized by the human immunophilin FKBP12 (Holt et al., *J. Am. Chem. Soc.* 1993, 115, 9925; incorporated herein by reference). Each of these compounds was attached to 400–450 µm diameter polystyrene beads (estimated capacity of 20 nmol per bead) via a 6-aminocaproic acid linker and either 4-methoxytrityl-protected cysteine (FIG. 6, X=S(Mmt)) or alanine (FIG. 6, X=H; negative control). To create reference points on the slides, beads were also prepared with a thiol-labeled derivative of the fluorescent dye tetramethylrhodamine (4a). Individual beads were placed in 28 separate wells of a 96-well plate and the compounds were deprotected, cleaved, and subsequently dissolved in 5 µL of DMF. The released compounds were then arrayed robotically onto a series of maleimide-derivatized glass slides with a distance of 300 µm between the centers of adjacent spots. Each slide was printed according to the pattern illustrated in FIG. 7D. Following a 12 hour room temperature incubation, the slides were washed extensively and probed with different proteins.

The slide in FIG. 7A was probed with Cy5-conjugated streptavidin, washed, and subsequently scanned using an ArrayWoRx fluorescence slide scanner. The slide was scanned for both tetramethylrhodamine fluorescence (false-colored green) and Cy5 fluorescence (false-colored red). As anticipated, only the spots containing 1a were visible when scanned for Cy5 fluorescence, indicating that localization of streptvidin on these spots was both specific for biotin and dependent on the thiol functionality (compound 1b, which lacks a thiol, does not attach to the slide). Using a two-step detection method, the slide in FIG. 7B was probed first with DI-22 and then with a Cy5-conjugated goat-anti-mouse antibody (which recognizes DI-22). As anticipated, the Cy5 fluorescence localized to the 2a-containing spots. Finally, the slide in FIG. 7C was probed using a three-step method: $(His)_6$-FKBP12 followed by mouse-anti-RGS$(His)_6$ antibody followed by Cy5-conjugated goat-anti-mouse antibody. As before, the fluorescence localized to the appropriate spots.

Figure 7:
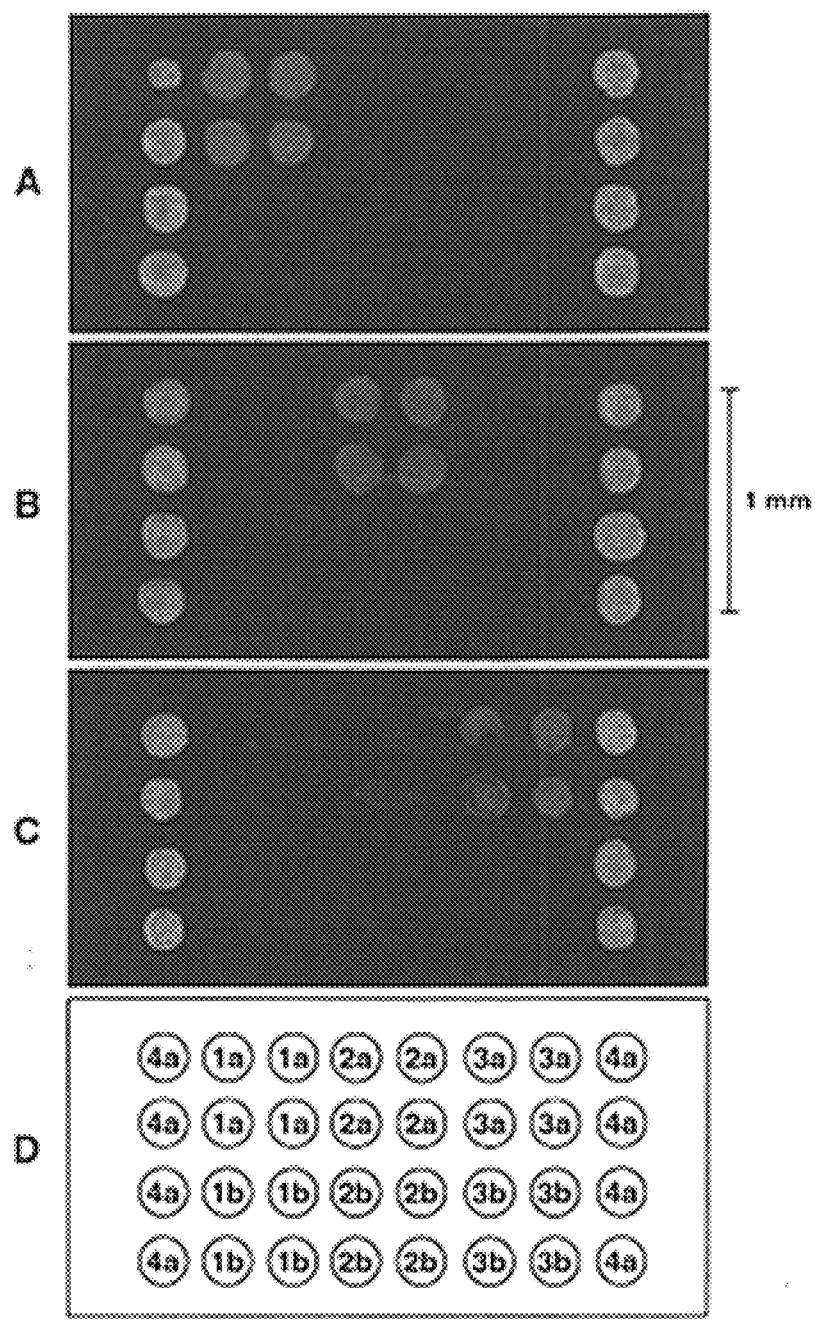
FIG. 7 depicts small molecules printed on maleimide-derivatized glass slides and detected with fluorophore-conjugated proteins. Compounds were printed according to the pattern illustrated in panel (D). Yellow circles indicate thiol-derivatized small molecule. (A) indicates a slide detected with Cy5-streptavidin. (B) indicates a slide detected with DI-22 followed by Cy5-goat-anti-mouse antibody. (C) indicates a slide detected with RGS $(His)_6$-FKBP12 followed by mouse-anti-RGS $(His)_6$ antibody followed by Cy5-goat-anti-mouse antibody.
Figure 8:
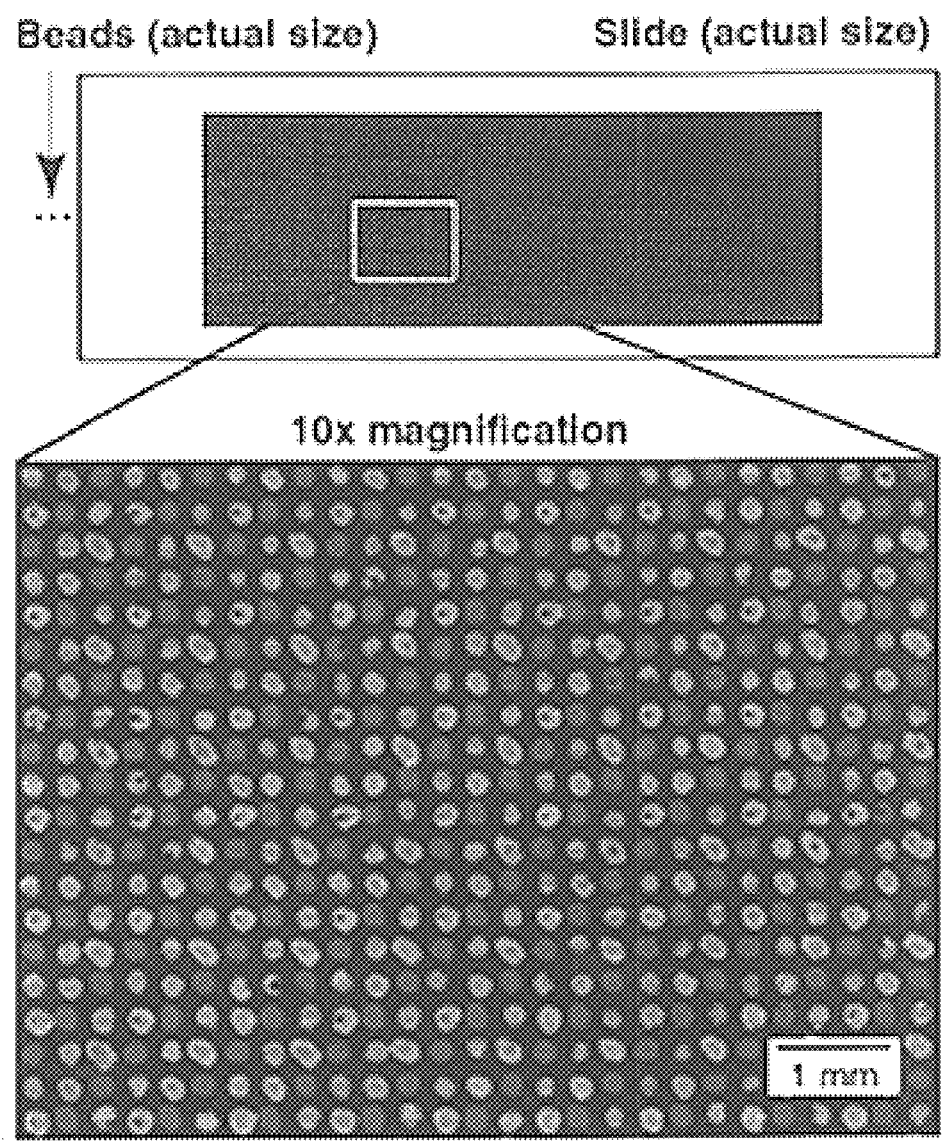
FIG. 8 depicts small molecules printed on a maleimide-derivatized glass slide and detected with FITC-streptavidin (blue), Cy3-DI-22 (green), and Cy5-FKBP12 (red). The full slide contains 10,800 distinct spots and was prepared using only one bead for each of the three small molecules printed (1a, 2a, and 3a as shown in FIG. 6).

These results clearly illustrate both the high selectivity and remarkable sensitivity of this slide-based assay. To illustrate the highly parallel nature of small molecule printing, compound 1a was released from a single 400–450 µm diameter polystyrene bead and the released compound was dissolved in 10 µL of DMF. We repeated this procedure for compounds 2a and 3a. Using the microarraying robot, these three compounds were repetitively spotted in an alternating pattern on a single maleimide-derivatized slide, using the same spatial density as in FIG. 7. Each compound was spotted 3600 times, using less than half of the compound from each bead (~1 nL per spot) and yielding 10,800 distinct spots. The slide was then probed in a single step with a solution containing FITC-conjugated streptavidin, Cy3-conjugated DI-22, and Cy5-conjugated FKBP12. Following a brief washing step, the slide was scanned for FITC fluorescence (false colored blue), Cy3 fluorescence (false-colored green), and Cy5 fluorescence (false-colored red). As shown in FIG. 8, the three differently labeled proteins localized to the spots containing their cognate ligands.

Experimental details for the above described example can be found in below. One of ordinary skill in the art will realize that the inventive compositions and methods are not limited to the examples described above; rather the present invention is intended to include all equivalents thereof.

Example 2
Small Molecule Printing Using Silylation Reaction

Figure 9:
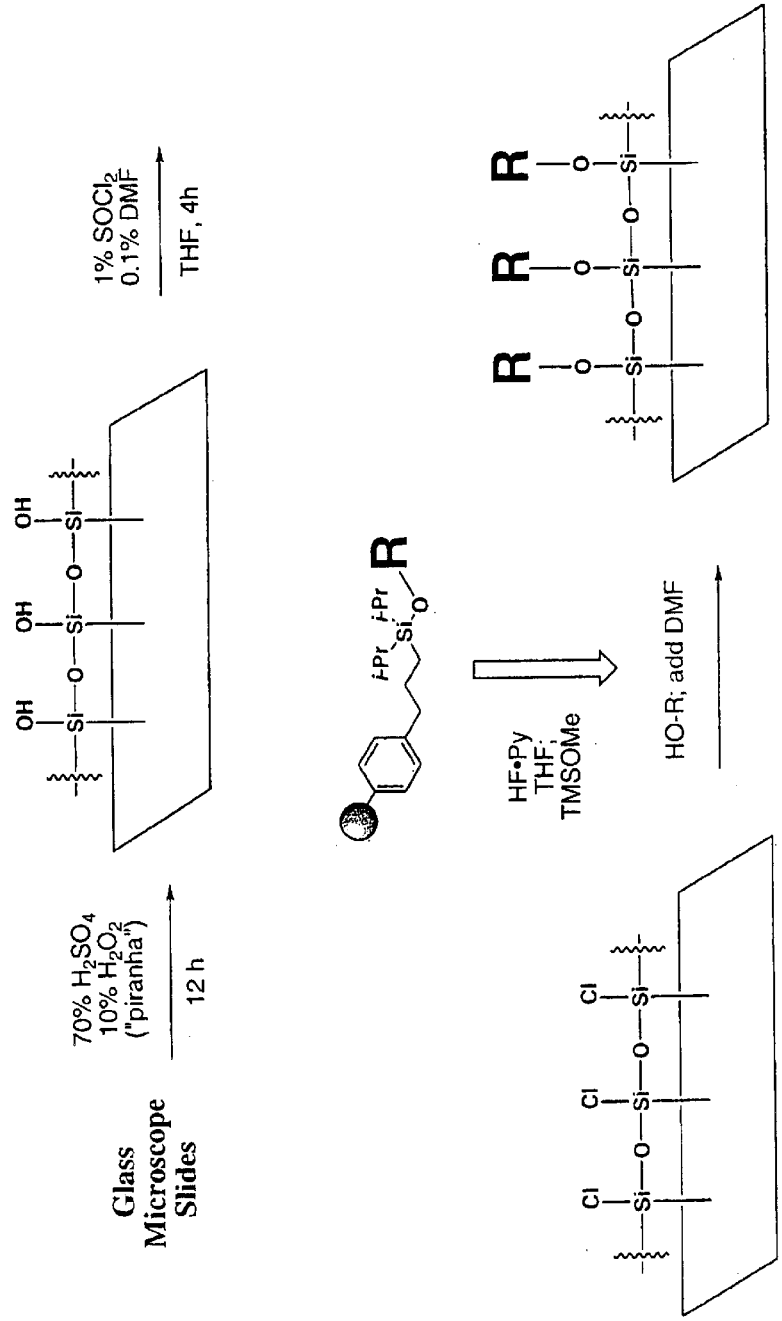
FIG. 9 shows the activation of glass slides for the covalent attachment of alcohols.

Standard glass slides were activated for selective reaction with alcohols (FIG. 9). Microscopic slides were first treated with a $H_2SO_4/H_2O_2$ solution ("piranha") for 16 hours at room temperature. After extensive washing with water, the slides were treated with thionyl chloride and a catalytic amount of DMF in THF for 4 hours at room temperature. Surface characterization by x-ray photoelectron spectroscopy (XPS) confirmed the presence of chlorine on the slide (Strother et al., J. Am. Chem. Soc., 2000, 122, 1205–1209; incorporated herein by reference). To test the ability of these chlorinated slides to capture alcohols released from synthesis beads, we initially used three alcohol-containing small molecules and a bead linker reagent developed for chemical genetic applications of diversity-oriented synthesis.

Primary alcohol derivatives of a synthetic α-ketoamide (Holt et al., J. Am. Chem. Soc. 1993, 115, 9925–9938; incorporated herein by reference), digoxigenin, and biotin were attached to silicon linker-modified beads (FIG. 10). These beads are high capacity 500–560 μm polystyrene beads equipped with an all hydrocarbon and silicon linker for the temporary attachment and eventual fluoride-mediated release of synthetic, alcohol-containing compounds. The three primary alcohol derivatives have known protein partners, namely FKBP12 (Harding et al., Nature, 1989, 341, 758–760; Siekierkea et al., Nature, 1989, 341, 755–757; each of which is incorporated herein by reference), the DI-22 antibody (Sigma), and streptavidin (Chaiet et al., Arch. Biochem. Biophys., 1964, 106, 1–5; incorporated herein by reference), respectively. After HF-pyridine-mediated release from the beads and subsequent solvent removal, the compounds were dissolved in 5 μL of DMF in individual wells of 96-well plates to give ~5 mM solutions. A microarrayer was used to spot the compounds (in triplicate) 400 μm apart (average spot diameter of 300 μm) onto the thionyl chloride-activated slides (FIG. 10b-e) and the slides were then washed extensively with DMF, THF, isopropanol, and an aqueous buffer. As shown, when binding was detected separately (FIG. 10b-d) or simultaneously (FIG. 10e), the recognition of the protein for its ligand was efficient and selective. When the same compounds were printed onto control slides (i.e., not activated with thionyl chloride) no protein-ligand interactions were detected.

Small molecules resulting from diversity-oriented syntheses can contain a wide array of functional groups, including secondary and phenolic hydroxyls. To test the ability of such functionalities to react with the thionyl chloride activated slides, the synthetic α-ketoamide derivatives shown in FIG. 11 were synthesized. An array was then printed (in quadruplicate) containing the primary, secondary, phenolic, and methyl ether derivatives at 18 5 mM, and probed with Cy5-FKBP. As shown in FIG. 11, the reaction of the primary alcohol is favored, and this bias holds even when the secondary, phenolic, and methyl ether derivatives are arrayed at a concentration ten times greater than the primary.

As a demonstration of the compatibility of this alcohol arraying technique with split-pool synthesis, a collection of 78 small molecules derived from such synthesis having the general structure shown in FIG. 12a was printed onto glass slides (Tan et al., J. Am. Chem. Soc. 1998, 120, 8565–8566; incorporated herein by reference). To this collection were added two members that had been acylated with the synthetic α-ketoamide derivative or biotin FIG. 12b). These 'tagged' members were then released from their beads, dissolved in 5 μL of DMF, and placed in known wells of a 96-well plate. After placing the 80 compounds into discrete wells, the entire plate was arrayed onto thionyl chloride/DMF activated slides, which were then probed with fluorescently-labeled proteins, Cy5-FKBP12 and FITC-streptavidin. The results (FIG. 12c) show that two spots in the array fluoresce in the Cy5 channel (false-colored red), and another fluoresces in the FITC channel (false-colored green). The positional encoding confirms the result that the compound acylated with the α-ketoamide was spotted in B8, and the compound acylated with biotin was spotted in F2. The spot visible in E3 is an apparent serendipitous and reproducible 'hit', and awaits further analysis. Thus, this experiment demonstrates the process of split-pool synthesis, release from the solid support, arraying onto glass slides, and detection/visualization of protein-small molecule binding events.

Example 3
Fabrication of Custom Slide Reaction Vessels

Figure 13:
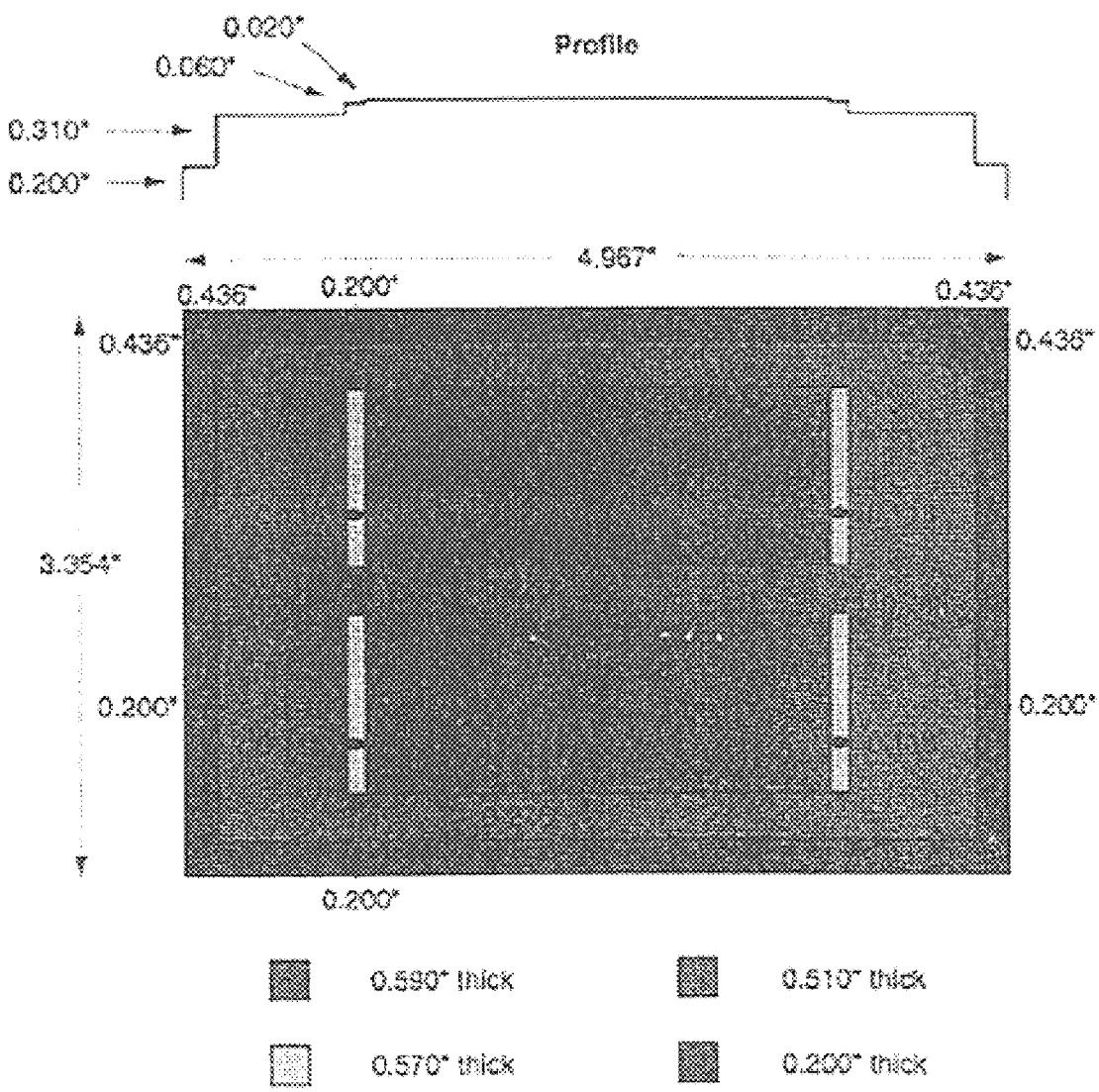
FIG. 13 shows the master template used to fabricate custom slide-sized reaction vessels that enable the uniform application of ~1.4 mL solution to one face of a 2.5 cm×7.5 cm slide.
Figure 14:
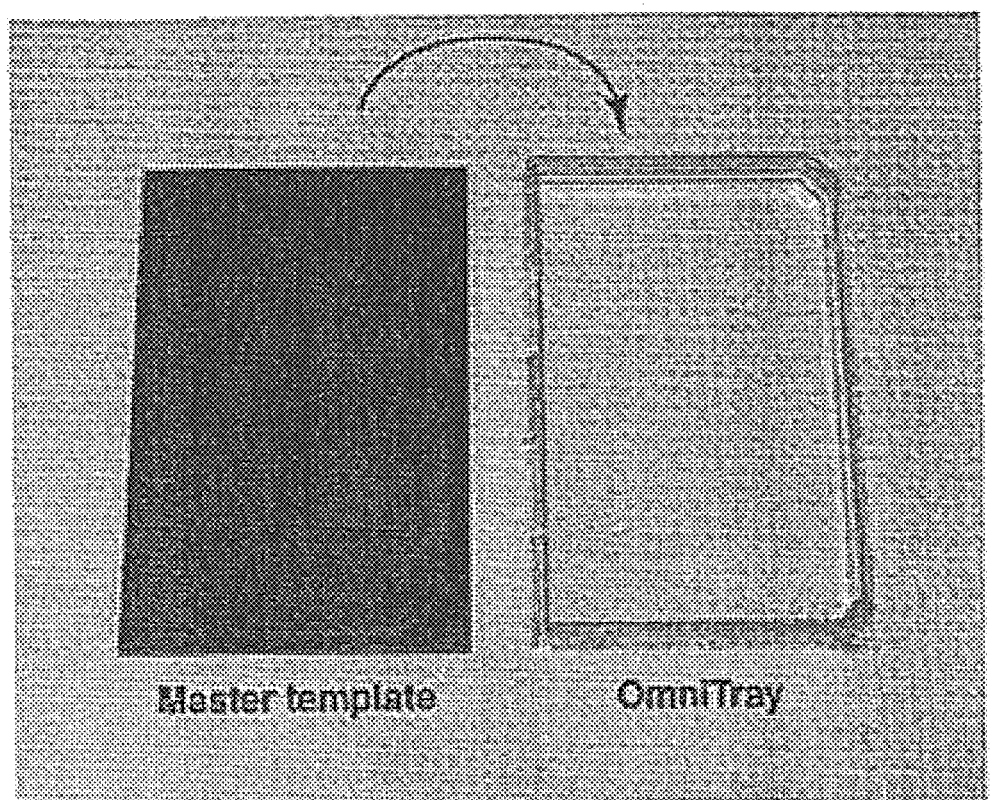
FIG. 14 shows the method of making the slide-sized reaction vessels.

In an effort to minimize reagent volume during the chemical treatment of glass microscope slides, we designed and fabricated custom slide-sized reaction vessels that enable the uniform application of ~1.4 mL solution to one face of a 2.5 cm×7.5 cm slide. First, a master template mold was cut from a block of Delhran plastic according to the blueprint shown in FIG. 13. The slide-sized reaction vessels were prepared by casting degassed polydimethysiloxane (PDMS, Sylgard Kit 184, Dow corning, Midland, Mich.) prepolymer around the master template in a polystyrene OmniTray (Nalge Nunc International, Naperville, Ill.). After curing for four hours at 65° C., the polymer was peeled away from the master to give the finished product (FIG. 14).

Figure 15:
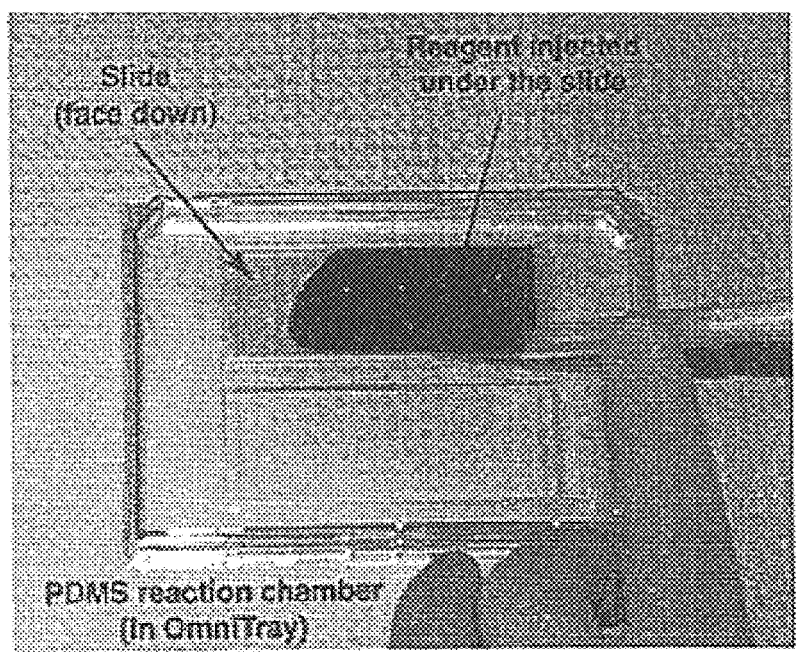
FIG. 15 shows the application of reagent to one surface of a slide.

To use the vessels, slides were placed face-down as illustrated below and reagent was injected under the slides with a P1000 Pipetman (FIG. 15).

Example 4
Chemical Derivatization of Glass Microscope Slides

Plain glass slides (VWR Scientific Products, USA) were cleaned in a "piranha" solution (70:30 v/v mixture of concentrated $H_2SO_4$ and 30% $H_2O_2$) for 12 hours at room temperature. (Caution: "piranha" solution reacts violently with several organic materials and should be handled with extreme care (Pintochovski et al., Electrochem. Soc. 1979, 126, 1428; Dobbs et al., Chem. Eng. News 1990, 68(17), 2; Wnuk, Chem. Eng. News 1990, 68(26), 2; Erickson, Chem. Eng. News 1990, 68(33), 2; each of which is incorporated herein by reference)). After thorough rinsing with distilled water, the slides were treated with a 3% solution of 3-aminopropyltriethoxysilane (United Chemical Technologies, Bristol, Pa.) in 95% ethanol for 1 hour. (Before treating the slides, the 3% silane solution was stirred for at least 10 minutes to allow for hydrolysis and silanol formation). The slides were then briefly dipped in 100% ethanol and centrifuged to remove excess silanol. The absorbed silane layer was cured at 115° C. for one hour. After cooling to room temperature, the slides were washed several times in 95% ethanol to remove uncoupled reagent.

A simple, semi-quantitative method was used to verify the presence of amino groups on the slide surface (Licitra et al., Proc. Natl. Acad. Sci. USA 1996, 93, 12817–12821; incorporated herein by reference). One glass slide from each batch of amino-functionalized slides was washed briefly with 5 mL of 50 mM sodium bicarbonate, pH 8.5. The slide was then dipped in 5 mL of 50 mM sodium bicarbonate, pH 8.5 containing 0.1 mM sulfo-succinimidyl-4-O-(4,4'-dimethoxytrityl)-butyrate (s-SDTB; Pierce, Rockford, Ill.) and shaken vigorously for 30 minutes. (The s-SDTB solution was prepared by dissolving 3.03 mg of s-SDTB in 1 mL of DMF and diluting to 50 mL with 50 mM sodium bicarbonate, pH 8.5). After a 30 minute incubation, the slide was washed three times with 20 mL of distilled water and subsequently treated with 5 mL of 30% perchloric acid. The development of an orange-colored solution indicated that the slide had been successfully derivatized with amines; no color change was seen for untreated glass slides. Quantitation of the 4,4'-dimethoxytrityl cation $\epsilon_{498nm}=70,000$ $M^{-1}$ $cm^{-1}$) released by the acid treatment indicated an approximate density of two amino groups per $nm^2$.

The resulting amino-functionalized slides were transferred to custom slide-sized polydimethylsiloxane (PDMS) reaction vessels (as described in Example 3). One face of each slide was treated with 20 mM N-succinimidyl 3-maleimido propionate (Aldrich Chemically Co., Milwaukee, Wis.) in 50 mM sodium bicarbonate buffer, pH 8.5, for three hours. (This solution was prepared by dissolving the N-succinimidyl 3-maleimido propionate in DMF and then diluting 10-fold with buffer). After incubation, the plates were washed several times with distilled water, dried by centrifugation, and stored at room temperature under vacuum until further use.

Example 5
Attachment of Small Molecules to Polystyrene Beads
Materials

Fmoc-εAhx-OH and 1,2-benzotriazolyloxy-tris [pyrrolidino]phosphonium hexafluorophosphate(PyBOP®) were from Novabiochem (San Diego, Calif.). Biotin and diisopropylethylamine (DIPEA) were from Aldrich Chemical Co. (Milwaukee, Wis.). 3-Amino-3-deoxydigoxigenin hemisuccinamide, succinimidyl ester and 5(6)-TAMRA, SE were from Molecular Probes (Eugene, Oreg.). Wash solvents were obtained from Mallinckrodt or E. Merck and used as received. Anhydrous dimethylformamide (DMF) was obtained from Aldrich Chemical Co. in SureSeal™ bottles.

The "FKBP Ligand" is shown below and was synthesized as published (Keenan et al., Bioorg. Med. Chem. 1998, 6, 1309; Amara et al., Proc. Natl. Acad. Sci. USA 1997, 94, 10618–10623; each of which is incorporated herein by reference).

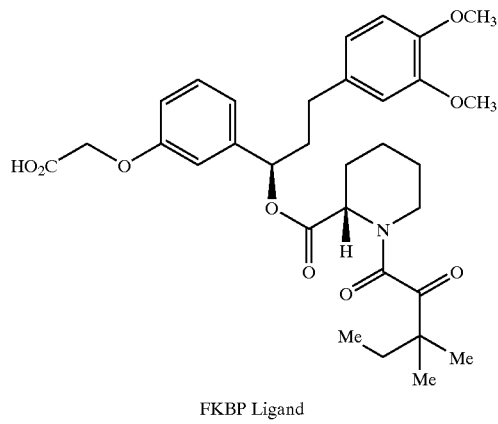

FKBP Ligand

Polystyrene synthesis beads were obtained by custom synthesis from Rapp Polymere (Tübingen, Germany). They ranged from 400 μm to 450 μm in diameter, had an estimated capacity of about 0.4 mmol/g (17 nmol/bead), and came functionalized as indicated below.

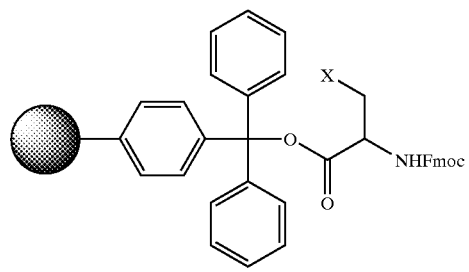

Polystyrene A Trt-Cys(Mmt) Fmoc: X = S(Mmt)
Polystyrene A Trt-Ala Fmoc: X = H

Solid Phase Reactions

Solid phase reactions were performed in either 2 mL fritted polypropylene Biospin® chromatography columns (Pharmacia Biotech, Uppsala, Sweden) or 10 mL fritted polypropylene PD-10 columns (Pharmacia Biotech). Resin samples were washed on a Val-Man® Laboratory Vacuum Manifold (Promega, Madison, Wis.) using the following procedure: 3×DMF, 3×THF, 3×DMF, 3×THF, 3×DMF, 3×THF, 3×DMF, 6×CH$_2$Cl$_2$, 3×THF.

Polystyrene Beads with Attached Linker (5c, 5d)

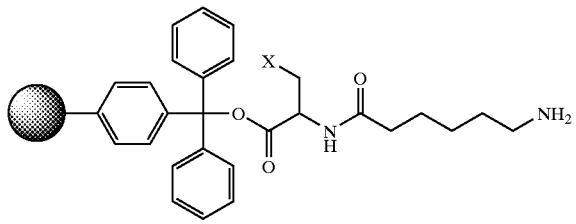

5c: X = S(Mmt)
5d: X = H

Either Polystyrene A Trt-Cyc(Mmt) Fmoc or Polystyrene A Trt-Ala Fmoc (400 mg, 0.4 mmol/g, 0.16 mmol) was placed in a 10 mL column and swollen with 6 mL DMF for 2 min. The column was drained and the Fmoc group removed by two 15 min treatments with 6 mL of 20% piperidine in DMF. The resin was washed (as described above), dried under vacuum, and swollen with 6 mL anhydrous DMF for 2 min. The column was drained and the resin swollen with 6 mL distilled CH$_2$Cl$_2$ for another 2 min. The column was drained and a mixture containing anhydrous DMF (5.2 mL), Fmoc-εAhx-OH (283 mg, 0.80 mmol, 5 eq), PyBOP® (416 mg, 0.80 mmol, 5 eq), and DIPEA (279 μL, 160 mmol, 10 eq) was added. After 12 h, the resin was washed and found to be negative to Kaiser ninhydrin test. The Fmoc group was then removed (as above) and the resin washed to give 5c and 5d.

Polystyrene Beads with Attached Linker and Biotin (1c, 1d)

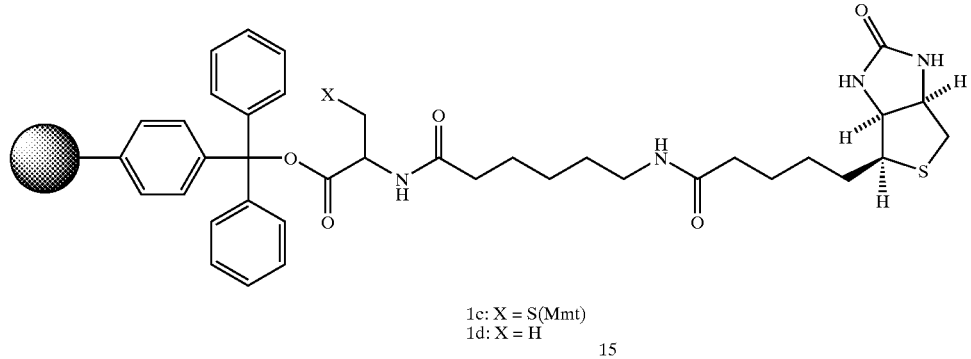

1c: X = S(Mmt)
1d: X = H

Either resin 5c or resin 5d (100 mg, 0.040 mmol, 1 eq) was placed in a 2 mL column and swollen with 1.5 mL anhydrous DMF for 2 min. The column was drained and the resin swollen with 1.5 mL distilled $CH_2Cl_2$ for another 2 min. The column was drained and a mixture containing anhydrous DMF (1.3 mL), biotin (39.1 mg, 0.16 mmol, 4 eq), PyBOP® (83.3 mg, 0.16 mmol, 4 eq), and DIPEA (55.7 μL, 0.32 mmol, 8 eq) was added. After 12 h, the resin was washed and subsequently found to be negative to Kaiser ninhydrin test.

Polystyrene Beads with Attached Linker and Digoxigenin Derivative (2c, 2d)

Either resin 5c or resin 5d (10 mg, 0.004 mmol, 1 eq) was placed in a 2 mL column and swollen with 1.5 mL anhydrous DMF for 2 min. The column was drained and the resin swollen with 1.5 mL distilled $CH_2Cl_2$ for another 2 min. The column was drained and a mixture containing anhydrous DMF (1.0 mL), 3-amino-3-deoxydigoxigenin hemisuccinamide, succinimidyl ester (5.0 mg, 0.0085 mmol, 2.1 eq), and DIPEA (20 μL, 0.115 mmol, 29 eq) was added. After 12 h, the resin was washed and treated for an additional 12 h with a fresh preparation of the mixture described above. The resin was washed again and subsequently found to be negative to Kaiser ninhydrin test.

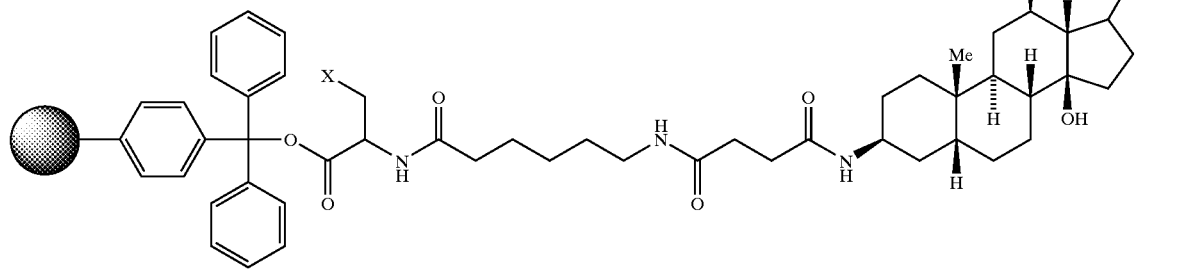

2c: X = S(Mmt)
2d: X = H

Polystyrene Beads with Attached Linker and FKBP Ligand (3c, 3d)

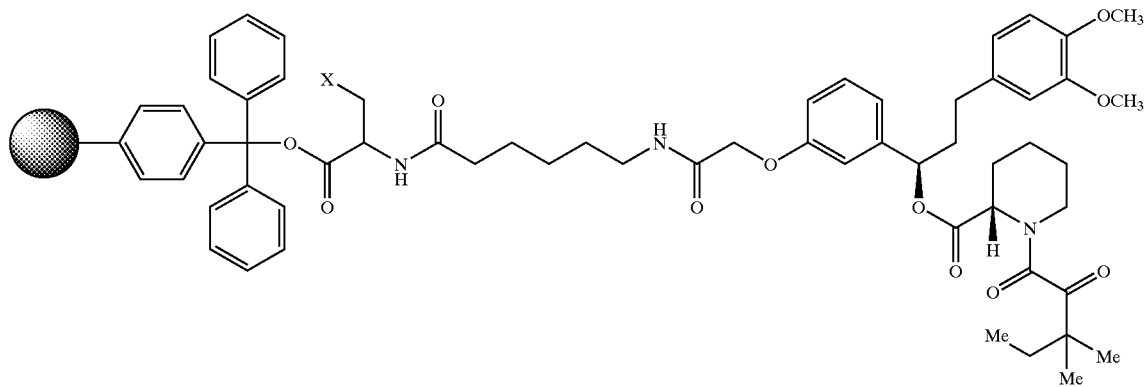

3c: X = S(Mmt)
3d: X = H

Either resin 5c or resin 5d (100 mg, 0.04 mmol, 1 eq) was placed in a 2 mL column and swollen with 1.5 mL anhydrous DMF for 2 min. The column was drained and the resin swollen with 1.5 mL distilled $CH_2Cl_2$ for another 2 min. The column was drained and a mixture containing anhydrous DMF (1.3 mL), FKBP ligand (67.5 mg, 0.116 mmol, 2.9 eq), PyBOP® (83.3 mg, 0.16 mmol, 4 eq), and DIPEA (55.7 μL, 0.32 mmol, 8 eq) was added. After 12 h, the resin was washed and subsequently found to be negative to Kaiser ninhydrin test.

Polystyrene Beads with Attached Linker and Tetramethylrhodamine Derivative (4c)

James S. Hardwick and Jeffrey K. Tong according to directions provided by Dr. Patrick O. Brown.

The robot was instructed to pickup a small amount of solution (~250 nL) from consecutive wells of a 96-well plate and repetitively deliver approximately 1 nL to defined locations on a series of maleimide-derivatized glass microscope slides. The pin used to deliver the compounds was washed with double distilled water for 8 s and dried under a stream of air for 8 s before loading each sample (6 s). Following printing, the slides were incubated at room temperature for 12 h and then immersed in a solution of 2-mercaptoethanol/DMF (1:99) to block remaining maleimide functionalities. The slides were subsequently washed for

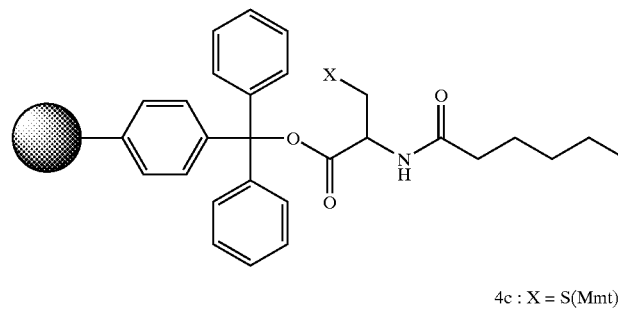
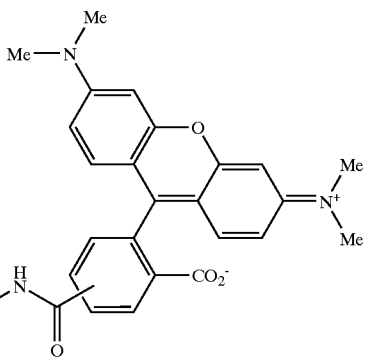

4c : X = S(Mmt)

Either resin 5c or resin 5d (40 mg. 0.016 mmol, 1 eq) was placed in a 2 mL column and swollen with 1.5 mL anhydrous DMF for 2 min. The column was drained and the resin swollen with 1.5 mL distilled $CH_2Cl_2$ for another 2 min. The column was drained and a mixture containing anhydrous DMF (1.0 mL), 5(6)-TAMRA, SE (25 mg, 0.047 mmol, 3.0 eq), and DIPEA (20 μL, 0.115 mmol, 7.2 eq) was added. After 12 h, the resin was washed and treated for an additional 12 h with a fresh preparation of the mixture described above. The resin was washed again to yield resin 4c.

Mass Spectrometry

As confirmation of this standard coupling chemistry, about 10 beads each of 1c, 1d, 2c, 2d, 3c and 3d were exposed to 100 μL of trifluoroacetic acid/triisopropylsilane/chloroform (2:1:17) for 2 h at room temperature. The deprotection/cleavage solution was then removed in vacuo and the liberated compounds dissolved in 20 μL DMF. FAB+MS gave molecular weights that exactly matched those predicted for compounds 1a, 1b, 2a, 2b, 3a and 3b, respectively.

Example 6
Small Molecule Printing
Deprotection and Release of Small Molecules

Individual beads (1c, 1d, 2c, 2d, 3c, 3d, 4c) were placed in separate wells of a polypropylene V-bottom 96-well plate (Costar, Corning, N.Y.) using an 18-gauge needle and a low power dissecting microscope. To each well was added 20 μL of trifluoroacetic acid/triethylsilane/chloroform (2:1:17) and the wells were immediately sealed with polyethylene strip caps (Nalge Nunc International, Naperville, Ill.). After 2 h at room temperature, the caps were discarded and the cleavage solution removed in vacuo. The released compounds were then dissolved in 5–10 μL of DMP and printed onto maleimide-derivatized glass slides.

Robotic Arraying of Small Molecules

Figure 16:
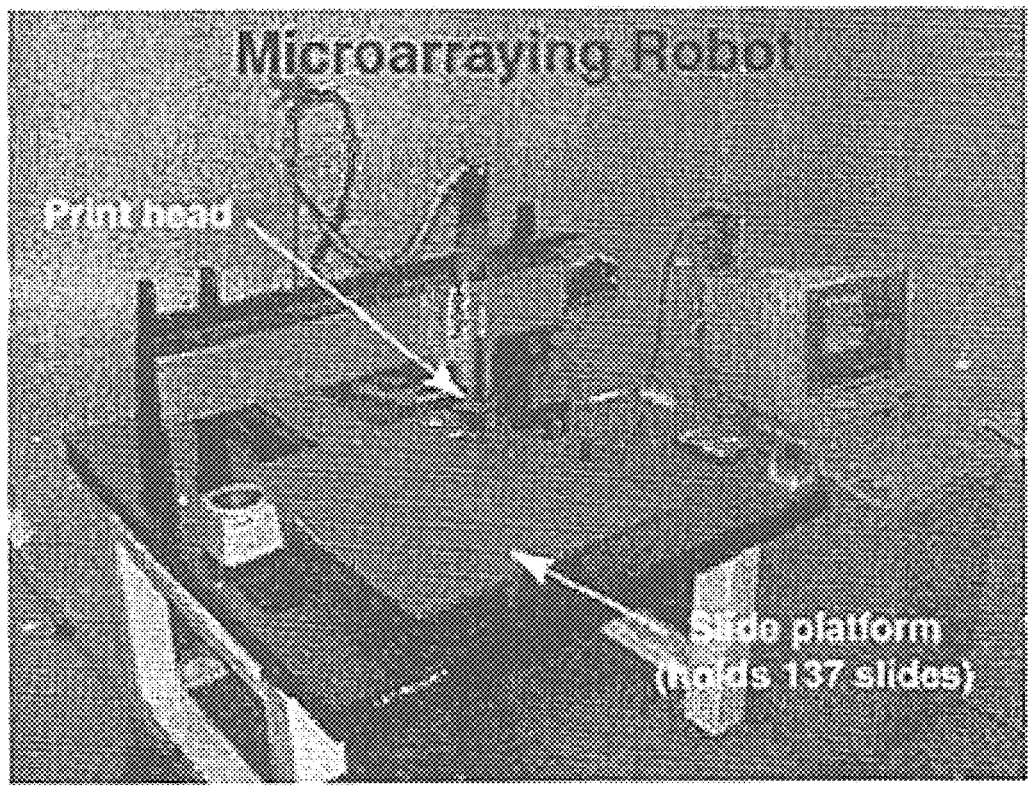
FIG. 16 shows the microarraying robot used to create the small molecule arrays.
Figure 17:
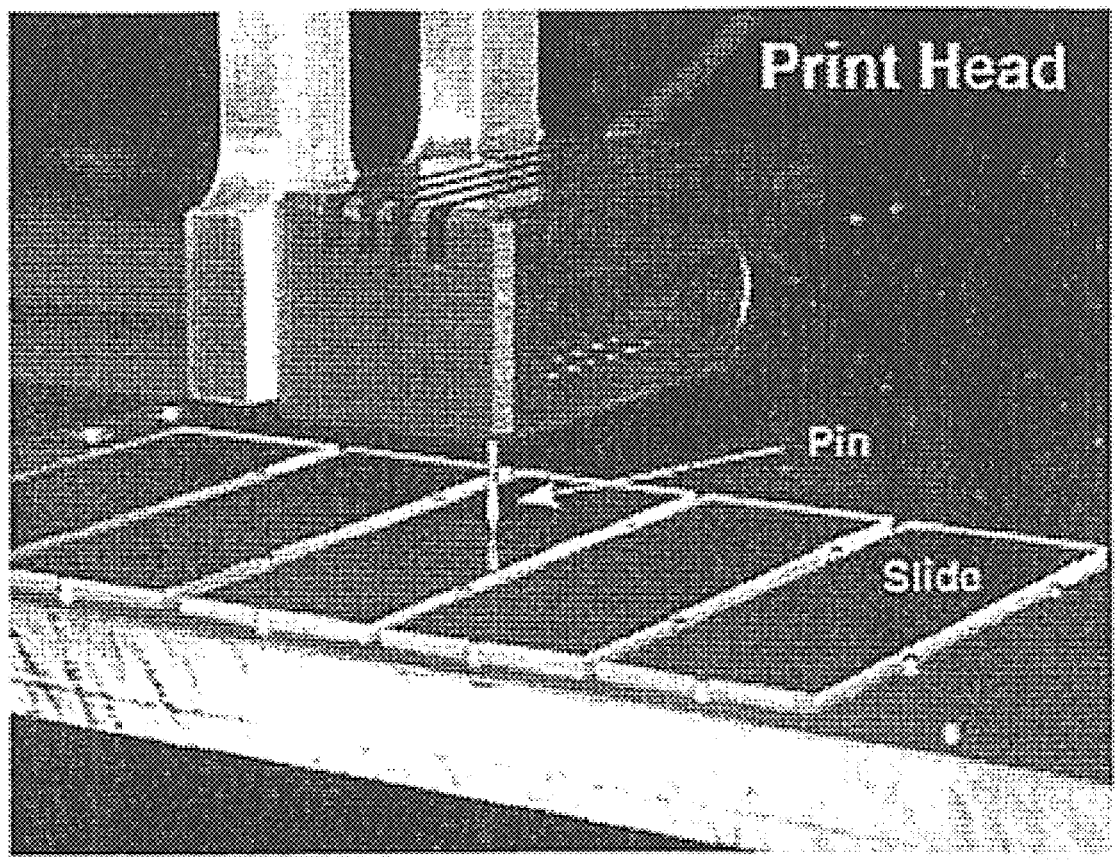
FIG. 17 shows the print head of the robot.
Figure 18:
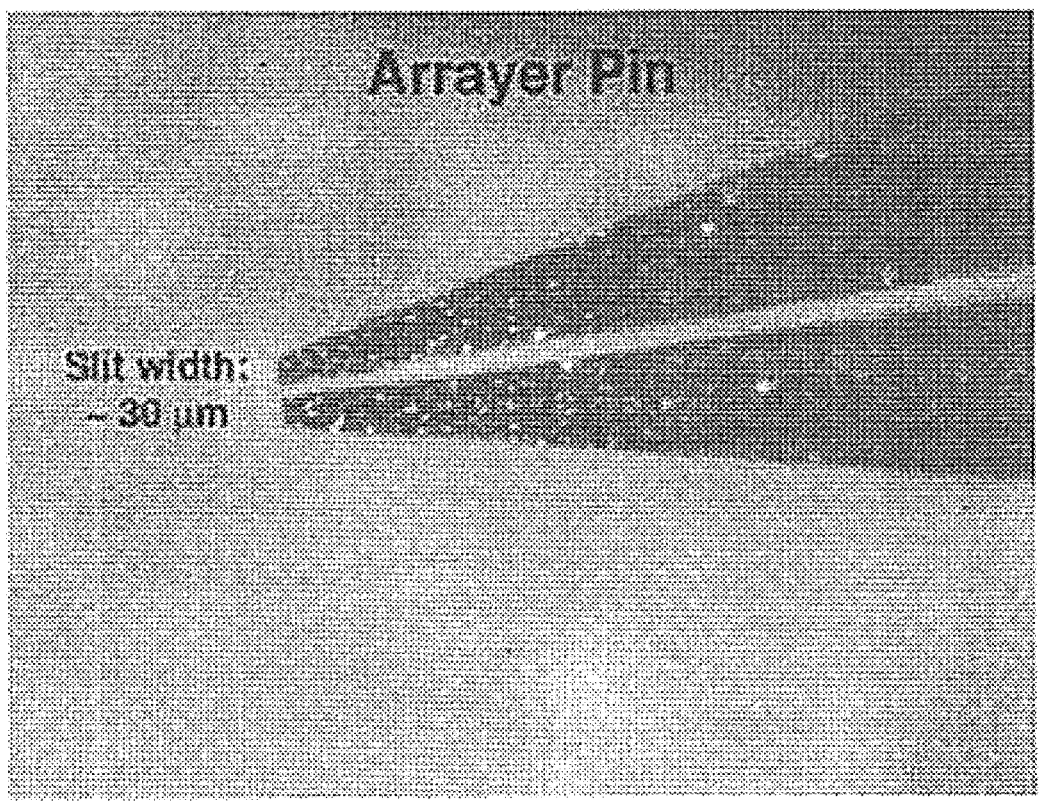
FIG. 18 shows the array pin of the robot.

Small molecules were printed using a microarraying robot (FIGS. 16, 17, and 18), constructed in this laboratory by Dr.

1 h each with DMF, THF, and iPrOH, followed by a 1 h aqueous wash with MBST (50 mM MES, 100 mM NaCl, 0.1% Tween® 20, pH 6.0). Slides were rinsed with doubledistilled water, dried by centrifugation, and either used immediately or stored at room temperature for several days without any observed deterioration.

Example 7
Detection of Protein-Small Molecule Interactions
Materials

Cy5-streptavidin, Cy5-goat-anti-mouse IgG, and FITC-streptavidin were from Kirkegaard & Perry Laboratories (Gaithersburg, Md.). Mouse-anti-digoxin IgG (DI-22) was from Sigma-Aldrich Co. (St. Louis, Mo.). Mouse-anti-(His)$_6$ IgG (RGS.His antibody) was from Qiagen (Hilden, Germany).

Production of (His)$_6$-FKBP12
Construction of T5 Expression Plasmid

A 355-bp PCR product containing the coding sequence for human FKBP12 was obtained using primers FKBP-1S(ACGTACGTGGATCCATGGGAGTGCAGTGGAAACCA) and FKBP-1N(ACGTACGTGTCGACTTATTCCAGTTTTAGAAGCTCCACATCGA) on template pJG-FKBP12 (Licitra et al., Proc. Natl. Acad. Sci. USA 1996, 93, 12817–12821; incorporated herein by reference). The 333-bp Bam HI-Sal I fragment of this product was then ligated with the 3434-bp Bam HI-Sal I fragment of pQE-30 (Qiagen) to yield the T5 expression plasmid pQE-30-FKBP12 (3757 bp).

Production and Purification of (His)$_6$ FKBP 12

The host stain for protein production was M15[pREP4] (Qiagen). Cells from a single colony were grown in 500 mL of LB medium supplemented with 100 μg/mL sodium ampicillin and 25 μg/mL kanamycin at 37° C. up to an OD$_{600}$ of 0.8. The culture was cooled to room temperature and isopropyl 1-thio-β-D-galactopyranoside (IPTG) was added to a final concentration of 1 mM. After 16 h induction at room temperature, the cells were harvested and resuspended in 20 mL of PBS (10 mM phosphate, 160 mM NaCl, pH 7.5) supplemented with 100 μM phenylmethanesulfonyl fluoride (PMSF). Following cell lysis by passage through a French press, insoluble material was removed by centrifugation (28000 g, 20 min, 4° C.) and the supernatant loaded onto a column packed with 5 mL of Ni-NTA agarose (Qiagen) that had been preequilibrated with PBS. The column was thoroughly washed with PBS containing 10 mM imidazole, and bound protein was subsequently eluted with PBS containing 250 mM imidazole. The sample was dialyzed extensively against PBS and stored at 4° C.

Labeling of Proteins with Fluorophores

Cy3-labeled DI-22 was prepared from DI-22 mouse ascites fluid (Sigma-Aldrich Co.) using FluoroLink™ Cy3™ bisfunctional reactive dye (Amersham Pharmacia Biotech, Piscataway, N.J.) according to the recommended protocol. Similarly, Cy5-labeled (His)$_6$-FKBP12 was prepared from purified (His)$_6$-FKBP12 using FluoroLink™ Cy5™ monofunctional reactive dye (Amersham Pharmacia Biotech) according to the recommended protocol.

Probing Slides with Proteins

Reagents were applied to the printed face of the slides using PDMS slide reaction chambers. Rinsing and washing steps were performed with the slides face up in the lids of pipet tip boxes.

In each experiment, the slides were blocked for 1 h with MBST supplemented with 3% bovine serum albumin (BSA). Following each step in the procedure, the slides were rinsed briefly with MBST before applying the next solution. With the exception of the blocking step, the slides were exposed to protein solutions for 30 min at room temperature. These solutions were prepared by diluting stock solutions of the appropriate protein(s) with MBST supplemented with 1% BSA. After the final incubation, the slides were rinsed once with MBST and then gently agitated with 4 changes of MBST over the course of 12 min. The slides were dried by centrifugation and stored in the dark at room temperature.

The protein concentrations used in the preparation of FIGS. 7 and 8 were as follows:

FIG. 7A:
  1 μg/mL Cy5-streptavidin
FIG. 7B:
  2 μg/mL DI-22 (IgG1)
  1 μg/mL Cy5-goat-anti-mouse IgG
FIG. 7C:
  40 μg/mL (His)$_6$-FKBP12
  2 μg/mL mouse RGS.His IgG
  1 μg/mL Cy5-goat-anti-mouse IgG
FIG. 8:
  2 μg/mL FITC-streptavidin,
  +0.2 μg/mL Cy3-DI-22 (IgG1)
  +4 μg/mL Cy5-(His)$_6$-FKBP12

Scanning Slides for Fluorescence

Slides were scanned using an ArrayWoRx™ slide scanner (AppliedPrecision, Issaquah, Wash.). Slides were scanned at a resolution of 5 μm per pixel. Double filters were employed for both the incident and emitted light. For the images in FIG. 7, tetramethylrhodamine fluorescence was observed using a Cy3/Cy3 excitation/emission filter set (1 s exposure) and Cy5 fluorescence was observed using a Cy5/Cy5 excitation/emission filter set (2 s exposure). For the image in FIG. 8, fluorescein fluorescence was observed using a FITC/FITC excitation/emission filter set (10 s exposure), Cy3 fluorescence was observed using a Cy3/Cy3 excitation/emission filter set (2 s exposure), and Cy5 fluorescence was observed using a Cy5/Cy5 excitation/emission filter set (5 s exposure). The full slide image (top) was stitched with 4-fold pixel reduction and the magnified image (bottom) was stitched with 2-fold pixel reduction.

Example 8

Covalent Attachment and Screening of Alcohol-Containing Small Molecules on Glass Slides General Procedures for Synthetic Transformations Methylene chloride, diisopropylethylamine and dimethylformamide were distilled under nitrogen from calcium hydride. Tetrahydrofuran (HPLC grade, Fisher, solvent keg) was dried by passing the solvent through two columns of activated alumina (A-2) (Phanghorn et al., *Organometallics* 1996, 15, 1518; incorporated herein by reference). All other reagents were obtained from commercial suppliers. Solution phase reactions were carried out in 2 dram vials with Teflon screw caps. Reactions were monitored by thin layer chromatography using 0.25 mm silica gel 60 $F_{254}$ plates from EM Science and visualized with ceric ammonium molybdate (CAM) stain. All compounds were purified using 230–400 mesh silica gel 60 from EM Science. Biotinol was prepared as previously described (Islam et al., *J. Med. Chem.* 1994, 37,293–304; incorporated herein by reference). The digoxigenin derivative as its N-hydroxysuccinimide ester was obtained from Molecular Probes Inc. The FKBP ligand (AP1497, an acid) was obtained from Dr. Kazunori Koide of Harvard University and from Ariad Pharmaceuticals (Keenan et al., *Bioorg. Med. Chem. Lett.* 1998, 6, 1309; incorporated herein by reference).

The solid support, 500–560 μm polystyrene 1% divinylbenzene (Rapp Polymere) was derivatized with a 3-(p-anisolyldiisopropylsilyl)-propyl linker (Woolard et al., *J. Org. Chem.* 1997, 62, 6102; incorporated herein by reference). The library members were obtained from Dr. Kouji Hattori (Harvard). The secondary alcohol of this scaffold was derivatized following the method of Tan et al. (*J. Am. Chem. Soc.* 1999, 121, 9073–9087; incorporated herein by reference). Solid phase loading reactions were run under an inert atmosphere in 2.0 mL polypropylene Bio-Spin® chromatography columns (Bio-Rad Laboratories, Hercules, Calif.; 732–6008) bearing a 3-way nylon stopcock (Bio-Rad; 732–8107) and mixed by 360° rotation on a Barnstead-Thermolyne Labquake Shaker™ (VWR 56264-306).

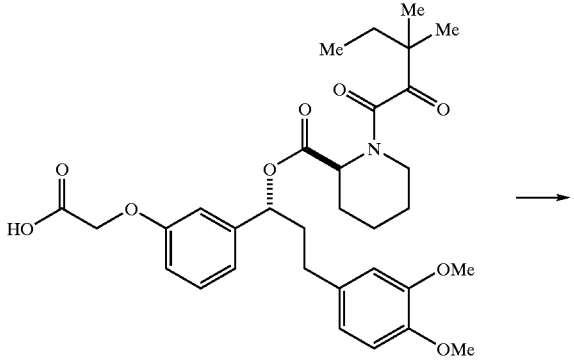

-continued

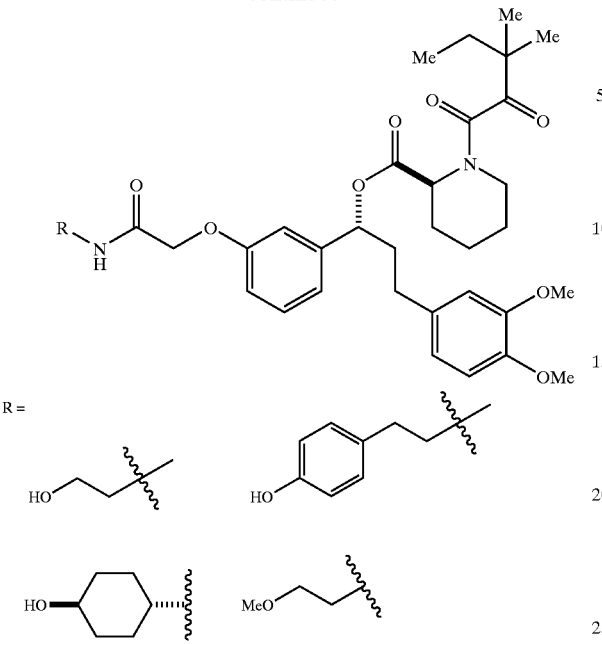

Representative Procedure for the Synthesis of the FKBP Ligands

To the above mentioned acid (17 mg, 0.029 mmol), in a solution of DMF (0.30 mL) was added the respective amine or amine hydrochloride (0.038 mmol), PyBOP (24.4 mg, 0.047 mmol), and i-Pr$_2$NEt (0.015 mL, 0.088 mmol, amines; 0.020 mL, 0.12 mmol, amine hydrochlorides). The solution was stirred at ambient temperature for 15 h, dissolved in a dilute brine solution and was extracted with EtOAc (3 times). The organic layers were combined, washed with a 1/1 water/saturated brine solution, dried over Na$_2$SO$_4$, filtered, concentrated, and chromatographed on silica gel (0 to 10% in CHCl$_3$) to give a colorless film.

primary OH (1) (reaction with ethanolamine); $^1$NMR (500 MHz, CDCl$_3$) δ 7.28 (m, 1H), 7.18 (m, 1 H NH), 6.98–6.66 (m, 6 H), 5.75 (dd, J=7.8, 5.4 Hz, 1 H), 5.29 (d, J=4.9 Hz, 1 H), 4.51 (m, 2 H), 3.85 (s, 3 H), 384 (s, 3 H), 3.72 (m, 2 H), 3.51 (m, 2 H), 3.35 (b d, J=13.2 Hz 1 H), 3.16 (td, J=12.3, 2.7 Hz, 1H), 2.56 (m,2 H), 2.36 (b d, J=13.7 Hz, 1 H), 2.23 (m, 1 H), 2.05 (m, 1 H), 1.77–1.62 (m, 6H), 1.48 (m, 1 H), 1.34 (m, 1H), 1.21 (s, 3H), 1.19 (s. 3 H), 0.87 (t, J=7.6 Hz, 3 H); HRMS (TOF-ES$^+$) calc. for C$_{34}$H$_{47}$N$_2$O$_9$ (M+H)$^+$, 627.3282, obs. 627.3306.

primary OMe (reaction with 2-methoxyethylamine); $^1$H NMR (500 MHz, CDCl$_3$) δ 7.30 (m, 1 H), 7.00–6.67 (m, 7 H), 5.76 (m, 1 H), 5.32 (d, J=4.9 Hz, 1 H), 4.51 (m, 2H), 3.86 (s, 3 H), 3.85 (s, 3 H), 3.55 (m, 2 H), 3.49 (m, 2H), 3.37 (d, J=13.0 Hz, 1 H), 3.35 (s, 3H), 3.16 (td, J=13.2, 2.9 Hz, 1H), 2.57 (m, 2 H), 2.36 (b d, J=13.7 Hz 1 H), 2.24 (m, 1H), 2.06 (m, 1 H), 1.79–1.58 (m, 6 H), 1.51–1.30 (m, 2 H), 1.23 (s, 3 H), 1.21 (s, 3H), 0.89 (t, J=7.6 Hz, 3 H); HRMS (TOF-ES$^+$) calc. for C$_{35}$H$_{48}$N$_2$O$_9$Na(M+Na)$^+$, 663.3258, obs. 663.3229.

secondary OH (reaction with trans-4-aminoyclohexanol hydrochloride); $^1$H NMR (500 MHz, CDCl$_3$) δ 7.29 (m, 1H), 6.99–666 (m, 6H), 6.41 (d, J=8.3 Hz, 1 H, NH), 5.76 (M, 1H), 5.30 (d, J=5.4 Hz, 1H), 4.46 (m, 2H), 3.85 (s, 3 H), 3.84 (s, 3H), 3.61 (m, 1 H), 3.36 (b d, J=12.2 Hz, 1 H), 3.20 TD, J=13.2, 2.9 Hz, 1 H), 2.56 (m, 2H), 2.36 (b d, J=13.7 Hz, 1 H), 2.24 (m, 1H), 2.00 (m, 4H), 1.78–1.61 (m, 6H), 1.50–1.23 (m, 4H), 1.21 (s, 3H), 1.20 (s, 3H), 0.88 (t, J=7.3 Hz, 3 H); HRMS (TOF-ES$^+$) calc. for C$_{38}$H$_{53}$N$_2$O$_9$(M+H)$^+$, 681.3751, obs. 681.3778.

phenolic OH (reaction with tyramine hydrochloride); $^1$H NMR (500 MHz, CDCl$_3$) δ 7.31 (m, 1 H), 7.01–66 (m, 10 H), 6.51 (m, 1 H, NH), 5.81 (m, 1 H), 5.33 (b d, J=5.1 Hz, 1 H), 4.60 (m, 2 H), 3.86 (s, 6 H), 3.55 (m, 2 H), 3.40 (b d, J=13.0 Hz 1 H), 3.27 (td, J=13.2, 2.9 Hz, 1H), 2.72 (t, J=6.4 Hz, 2 H), 2.56 (m, 2 H), 2.40 (b d, J=13.2 Hz, 1 H), 2.24 (m, 1 H), 2.06 (m, 1 H), 1.87–1.64 (m, 6 H), 1.54 (m, 1 H), 1.40 (m, 1 H), 1.24 (s, 3 H), 1.21 (s, 3 H), 0.88 (t, J=7.5 Hz, 3 H); HRMS (TOF-ES$^+$) calc. for C$_{40}$H$_{50}$N$_2$O$_9$Na(M+Na)$^+$, 725.3414, obs. 725.3384.

Procedure for the Digoxigenin Derivative

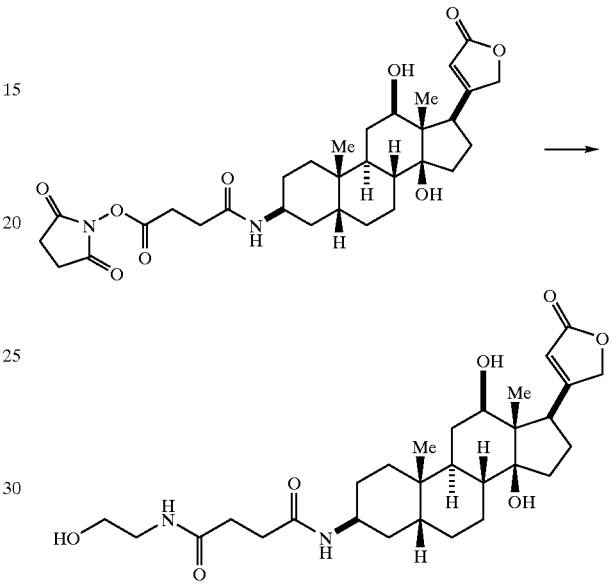

To a solution of the NHS ester of the digoxigenin derivative (5.0 mg, 0.0085 mmol) in DMF (0.3 mL) was added ethanolamine (0.0008 mL, 0.013 mmol) and 4-methylmorpholine (0.0011 mL, 0.010 mmol). The reaction was stirred at ambient temperature for three days, concentrated under high vacuum at room temperature, and chromatographed on silica gel (0 to 20% MeOH in CHCl$_3$); $^1$H NMR (400 MHz, 5/1 CDCl$_3$/CD$_3$OD) δ 5.84 (s, 1H), 4.81 (AB d, 2 H), 4.00 (b s, 1 H) 3.55 (m, 2H) 3.24 (m, 3H), 2.39 (m, 4 H), 2.04 (m, 1 H), 1.81 (4 H), 1.70–1.38 (m, 9H), 1.16 (m, 6 H), 0.88 (s, 3H), 0.67 (s, 3H).

General Procedure for Loading Alcohols via a Silicon Ether onto Polystyrene Beads After drying under vacuum for 8 h, the large polystyrene beads bearing a 3-(p-anisolyldiisopropylsilyl)-propyl linker (13.3 mg,0.008 mmol, ca. 0.6 mmol silane/g resin) were added to a Bio-Rad tube, which was capped with a septum and a plastic stopcock and flushed with an inert gas. The tube was then charged via syringe with a 2.5% (v/v) solution of TMS-Cl in CH$_2$Cl$_2$ The beads were suspended for 15 min, and filtered with inert gas pressure. The beads were washed with CH$_2$Cl$_2$ (0.5 mL, 3 times, 2 min/rinse) and then suspended in a 3% (v/v) solution of triflic acid in CH$_2$Cl$_2$ (0.142 mL, 0.049 mmol) for 15 min during which time the tube was shaken periodically. The beads turn a dark brown color. The beads were suspended and rinsed with CH$_2$Cl$_2$ (0.5 mL, 3 times, 2 min/rinse) under an inert gas, and left suspended in the fourth volume of CH$_2$Cl$_2$ Freshly distilled 2,6-lutidene (0.007 mL, 0.064 mmol) was added (the brown color disappears) and the azeotropically dried (from benzene) alcohol (0.020 mmol) was added as a solution in CH$_2$Cl$_2$ via a canula transfer (for α-ketoamide and digoxigenin, 3 volumes, 0.3 mL/transfer) or introduced as a neat solid (e.g, biotinol, when the alcohol is not soluble in $CH_2Cl_2$). The tube was capped and tumbled at ambient temperature for 2–4 h. The beads were then filtered, suspended, and rinsed, for α-ketoamide, with $CH_2Cl_2$ (10 times, 5 min/rinse) and dried under high vacuum; for digoxigenin and biotin, the beads were rinsed likewise with DMF to remove non-covalently attached ligand.

Activation of Slides for Microarraying

Slides were activated for covalent attachment of alcohols as follows. Standard microscope slides (VWR) were immersed in 70/30 (v/v) $H_2SO_4$/30% $H_2O_2$ (piranha) for 16 h at ambient temperature. After removal from the piranha bath, the slides were washed extensively in dd$H_2O$, and then kept under water until use. To convert to the silyl chloride, the slides were first removed from the water and dried by centrifugation. At this point, the slides were immersed in a solution of THF containing 1% $SOCl_2$ and 0.1% DMF. The slides were incubated in this solution for 4 h at ambient temperature. The slides were then removed from the chlorination solution, washed briefly with THF, and placed on the microarrayer.

Release of Alcohols from Their Solid Supports

To liberate alcohols from the polystyrene beads, single beads were treated with 10 μL of 90/5/5 (v/v) TBF/HF.pyridine/pyridine at ambient temperature for 1 h. 10 μL of TMSOMe was then added, and allowed to stand at ambient temperature for an additional 0.5 h. The solvent was then removed in vacuo, and the liberated compound from a single bead was dissolved in 5 μL of DMF. These solutions were then robotically arrayed onto activated glass slides.

We confirmed the coupling of the α-ketoamide and biotin to the secondary alcohol of the library by LC/LRMS (TOF-ES$^+$) analysis of material released from a single bead of each type. The observed ions (M+H)$^+$ of 1064 and 725 matched the theoretical masses expected for $C_{59}H_{75}N_4O_{14}$ (α-ketoamide) and $C_{37}H_{50}N_5O_8S$ (biotin), respectively.

Robotic Printing

Compounds were arrayed onto glass slides using a DNA microarrayer constructed by Dr. James Hardwick and Jeff Tong following instructions on the web site of Professor Patrick Brown (Stanford University). The microarrayer typically picks up 250 nL from the 96-well plate and delivers 1 nL drops onto the slides. These spots were placed 400 μm apart on the slides.

Detection of Protein/ligand Interactions

After arraying, the slides were allowed to incubate at ambient temperature for 12 h. The slides were then washed for 2 h with DMF, and 1 h each with THF, isopropanol, and MBST (50 mM MES, 100 mM NaCl, 0.1% Tween-20, pH=6.0). The slides were then blocked for 1 h by incubation with MBST containing 3% BSA. After a brief rinse with MBST, the fluorescently labeled protein was then added at a concentration of 1 μg/mL in MBST supplemented with 1% BSA. The labeled proteins were created as described (Tan et al., *J. Am. Chem. Soc.* 1999, 121, 9073–9087; MacBeath et al., *J. Am. Chem. Soc.* 1999, 121, 7967–7968; each of which is incorporated herein by reference). The slide was incubated with the labeled protein for 0.5 h at ambient temperature. At this point, the slide was washed (10 times 1 mL with MBST, then briefly with $H_2O$) and dried by centrifugation. The slide was then scanned using an ArrayWoRx slide scanner (AppliedPrecision, Issaquah, Wash.) at a resolution of 5 μm per pixel. The following filter sets were employed: Cy5/Cy5 excitation/emission filter set (2 s exposure); Cy3/Cy3 excitation/emission filter set (1 s exposure); FITC/FITC excitation emission filter set (10 s exposure).

Other Embodiments

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

What is claimed is:

1. An array comprising a plurality of more than one type of non-oligomeric compounds attached to a solid support,
   wherein the density of said array of compounds is at least 1000 spots per cm$^2$; and
   wherein the compounds are attached to the solid support as depicted:

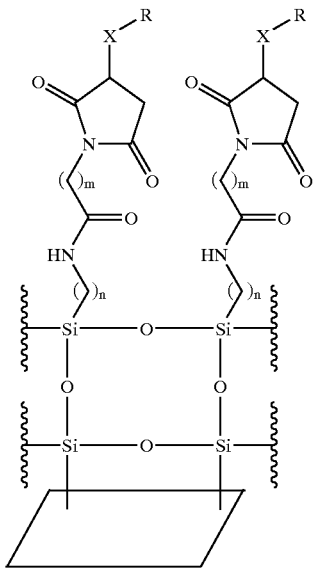

wherein

X is O, S, or NH;

m is an integer between 0 and 5;

n is an integer between 0 and 5; and

R is the compound attached to the solid support.

2. The array of claim 1, wherein said array of chemical compounds comprises an array of non-peptidic and non-oligomeric chemical compounds.

3. The array of claim 1, wherein each of said chemical compounds in said array is attached to the solid support through a covalent interaction.

4. The array of claim 1, wherein said covalent interaction is characterized in that the linkage is robust enough so that the compounds are (1) not inadvertently cleaved during subsequent manipulation steps and (2) inert so that the functionalities employed do not interfere with subsequent manipulation steps.

5. The array of claim 1, wherein each of said chemical compounds in said array is attached to the solid support through a linkage generated by a Michael addition.

6. The composition of claim 1, wherein the solid support is glass.

7. The array of claim 1, wherein said array of chemical compounds comprises an array of small molecules.

8. The array of claim 1, wherein the density of said array of compounds is at least 5000 spots per cm$^2$.

9. The array of claim 1, wherein the density of said array of compounds is at least 10,000 spots per cm$^2$.

* * * * *

SEQUENCE LISTING

<160> NUMBER OF SEQ ID NOS: 2

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence:PCR Primer
      for Human FKBP12

<400> SEQUENCE: 1
acgtacgtgg atccatggga gtgcaggtgg aaacca                          36

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence:PCR Primer
      for Human FKBP12

<400> SEQUENCE: 2
acgtacgtgt cgacttattc cagttttaga agctccacat cga                  43